United States Patent
Murphy et al.

(10) Patent No.: US 10,195,313 B2
(45) Date of Patent: Feb. 5, 2019

(54) METHOD FOR FORMING HYDROGEL ARRAYS USING SURFACES WITH DIFFERENTIAL WETTABILITY

(71) Applicant: Wisconsin Alumni Research Foundation, Madison, WI (US)

(72) Inventors: William L. Murphy, Waunakee, WI (US); Ngoc Nhi Thi Le, Madison, WI (US); Stefan Zorn, Madison, WI (US); Michael P. Schwartz, Madison, WI (US); Eric Huy Dang Nguyen, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 454 days.

(21) Appl. No.: 14/339,938

(22) Filed: Jul. 24, 2014

(65) Prior Publication Data
US 2015/0293073 A1 Oct. 15, 2015

Related U.S. Application Data

(60) Provisional application No. 61/978,032, filed on Apr. 10, 2014.

(51) Int. Cl.
| | |
|---|---|
| G01N 33/483 | (2006.01) |
| A61L 31/14 | (2006.01) |
| C12N 5/0735 | (2010.01) |
| G01N 33/50 | (2006.01) |
| A61K 47/42 | (2017.01) |
| A61L 29/16 | (2006.01) |
| B01J 19/00 | (2006.01) |
| G01N 21/64 | (2006.01) |

(52) U.S. Cl.
CPC ............ *A61L 31/145* (2013.01); *A61K 47/42* (2013.01); *A61L 29/16* (2013.01); *C12N 5/0606* (2013.01); *G01N 33/4833* (2013.01); *G01N 33/5005* (2013.01); *A61L 2300/80* (2013.01); *B01J 19/0046* (2013.01); *B01J 2219/00596* (2013.01); *C12N 2533/20* (2013.01); *C12N 2533/30* (2013.01); *C12N 2537/10* (2013.01); *G01N 21/6452* (2013.01); *G01N 2610/00* (2013.01)

(58) Field of Classification Search
CPC .................................................... A61L 31/145
USPC ............................................................ 506/9
See application file for complete search history.

(56) References Cited

U.S. PATENT DOCUMENTS

| | | | | |
|---|---|---|---|---|
| 2005/0019843 | A1* | 1/2005 | Chen ................ | G01N 33/56966 435/7.21 |
| 2007/0217019 | A1* | 9/2007 | Huang ................ | G02B 3/0031 359/642 |
| 2012/0149781 | A1 | 6/2012 | Lee et al. | |
| 2012/0225814 | A1 | 9/2012 | Hanijaya-Putra et al. | |
| 2013/0210147 | A1 | 8/2013 | Jeannin et al. | |
| 2013/0260464 | A1 | 10/2013 | Vannier et al. | |
| 2013/0296177 | A1 | 11/2013 | Koepsel et al. | |
| 2014/0017284 | A1 | 1/2014 | Yang et al. | |
| 2014/0018263 | A1* | 1/2014 | Levkin ................ | C12N 11/08 506/26 |
| 2015/0104812 | A1* | 4/2015 | Grevesse ................ | A61L 27/52 435/7.21 |

FOREIGN PATENT DOCUMENTS

WO       2011156686 A2    12/2011

OTHER PUBLICATIONS

Pishko, M. (Engineering in Medicine and Biology, 27th Annual Conference, Shanghai, China, Sep. 1-4, 2005, pp. 1058-1064).*
Hern et al. (Journal of Biomed Mater Res, 1998, 39(2), pp. 266-276).*
Heller (Annual Reviews of Biomedical Engineering, 2002, 4:129-153) (Year: 2002).*
Kyburz et al., Three-dimensional hMSC motility within peptide-functionalized PEG-based hydrogels of varying adhesivity and crosslinking density, Acta Biomaterialia, vol. 9, No. 5, pp. 6381-6392, 2013.
Leslie-Barbick et al., The promotion of microvasculature formation in poly(ethylene glycol) diacrylate hydrogels by an immobilized VEGF-mimetic peptide, Biomaterials, vol. 32, No. 25, pp. 5782-5789, 2011.
Love et al., Self-Assembled Monolayers of Thiolates on Metals as a Form of Nanotechnology, Chem. Rev. 2005, 105:1103-1169.
Strother et al., Synthesis and Characterization of DNA-Modified Silicon (III) Surfaces, J. Am. Chem. Soc. 2000, 122:1205-1209.

(Continued)

*Primary Examiner* — Karla A Dines
(74) *Attorney, Agent, or Firm* — Stinson Leonard Street LLP

(57) ABSTRACT

Patterned hydrogel arrays and methods of preparing patterned hydrogel arrays are disclosed. Advantageously, the methods used to prepare the patterned hydrogel arrays allow for controlling individual hydrogel spot conditions such as hydrogel spot modulus, hydrogel spot ligand identity and hydrogel spot ligand density, which allows for preparing a wide range of hydrogel spots in a single array format. Patterned hydrogel arrays can also be formed to include hydrogel-free pools surrounded by hydrogel. Additionally, the patterned hydrogel arrays of the present disclosure support the culture of a range of cell types. The patterned hydrogel arrays offer the ability to rapidly screen substrate components for influencing cell attachment, spreading, proliferation, migration, and differentiation.

20 Claims, 14 Drawing Sheets

Specification includes a Sequence Listing.

(56) References Cited

OTHER PUBLICATIONS

Schwartz et al., Chemical modification of silicon surfaces for biological applications, 2005 Phys. Stat. Sol. (a) 202 (8):1380-1384.
Strother et al., Photochemical Functionalization of Diamond Films, Langmuir, 2002, 18:968-971.
Polizzotti et al., Three-Dimensional Biochemical Patterning of Click-Based Composit Hydrogels via Thiolene Photopolymerization, Biomacromolecules 2008, 9:1084-1087.
Fairbanks et al., a Versatile Synthetic Extracellular Matrix Mimic via Thiol-Norbornehe Photopolymerization, Adv. Mater. 2009, 21:5005-5010.
Nagase and Fields, Human Matrix Metalloproteinase Specificity Studies Using Collagen Sequence-Based Synthetic Peptides, Biopolymers 1996, 40:399-416.
Toepke et al., Characterization of Thiol-Ene Crosslinked PEG Hydrogels, 2013, Macromol. Mater. Eng., 298:699-703.
Impellitteri et al., Specific VEGF sequestering and release using peptide-functionalized hydrogel microspheres, Biomaterials 2012, 33:3475-84.
Belair and Murphy, Specific VEGF sequestering to biomaterials: Influence of serum stability, Acta Biomater, 2013.
Gould et al., Small Peptide Functionalized Thiol-Ene Hydrogels as Culture Substrates for Understanding Valvular Interstitial Cell Activation and de novo Tissue Deposition, Acta Biomater 2012, 8:3201-3209.
Seo et al., Attachment of hydrogel microstructures and proteins to glass via thiol-terminated silanes, Colloids Surf B . Biointerfaces 2012, 98:1-6.
Halliwell et al., A Factorial Analysis of Silanization Conditions for the Immobilization of Oligonucletotides on Glass Surfaces, Anal Chem 2001, 73:2476-2483.
Cras et al., Comparison of chemical cleaning methods of glass in preparation for silanization, Biosens Bioelectron 1999, 14:683-688.
Vistas et al., Silanization of glass chips—A factorial approach for optimization, Appl Surf Sci 2013, 286:314-318.
Jo et al., Three-Dimensional Micro-Channel Fabrication in Polydimethylsiloxane (PDMS) Elastomer, 2000 J Microelectromechanical Syst. 9:76-81.
Prime and Whitesides, Adsorption of Proteins onto Surfaces Containing End-Attached Oligo(ethylene oxide): A Model System Using Self-Assembled Monolayers, 1993 J. Am. Chem. Soc. 115:10714-10721.
Engler et al., Matrix Elasticity Directs Stem Cell Lineage Specification, Cell 126:677 (2006).
Nguyen et al. "Differential effects of cell adhesion, modulus and VEGFR-2 inhibition on capillary network formation in synthetic hydrogel arrays," Biomaterials, 35, 2014, pp. 2149-2161.
Hansen et al., "Biomaterial arrays with defined adhesion ligand densities and matrix stiffness identify distinct phenotypes for tumorigenic and non-tumorigenic human mesenchymal cell types," Biomaterials Science, Royal Society of Chemistry, Published Jan. 22, 2014, 12 pages.
Banerjee, et al., The influence of hydrogel modulus on the proliferation and differentiation of encapsulated neural stem cells, Biomaterials, 2009, vol. 30, No. 27, pp. 4695-4699.
Engler et al., Matrix Elasticity Directs Stem Cell Lineage Specification, Cell, vol. 126, pp. 677-689, (2006).
Raza, et al., The influence of matrix degradation and functionality on cell survival and morphogenesis in PEG-based hydrogels, Macromolecular Bioscience, 2013, vol. 13, No. 8, pp. 1048-1058.
Porter et al., Covalently grafted VEGF 165 in Hydrogel models upregulates the cellular pathways associated with angiogenesis, Am I Physiol Cell Physiol, vol. 301, pp. C1086-C1092, 2011.
Shih, et al., Cross-Linking and Degradation of Step-Groth Hydrogels Formed by Thiol-Ene Photoclick Chemistry, Bio Macromolecules, 2012, pp. 2003-2012.
Liu, et al., Covalently immobilized biomolecule gradient on hydrogel surface using a gradient generating microfluidic device for a quantitative mesenchymal stem cell study, Biomicrofluidics 6, 024111, 2012.
Schwartz et al., Synthetic extracellular matrix for investigating 3D vascular network formation; National Institutes of Health; National Science Foundation; 1-page.
Schwartz et al., Synthetic extracellular matrix for investigating 3D vascular network formation; Depts. of 1. Biomedical Engineering. 2. Orthopedics and Rehabilitation, and 3. Cell and Regenerative Biology, University of Wisconsin-Madison; 4. Morgridge Institute for Research, Madison, WI 5. Department of Molecular, Cellular, and Developmental Biology, University of Californa-Santa Barbara, 1-page.
Zhang et al., Vascular differentiation of bone marrow strem cells is directed by a tunable three-dimensional matrix, Acta Biomaterialia; 2010, pp. 3395-3403.
Heller, M.J.; DNA Microarray Technology: Devices, Systems, and Applications. Aricle in Annual Review of Biomedical Engineering, Feb. 2002; 29 pages.
Kharkar, et al., Designing degradable hydrogels for orthogonal control of cell microenvironments, Chem. Cos. Rev., 2013, vol. 42, pp. 7335-7372.

\* cited by examiner

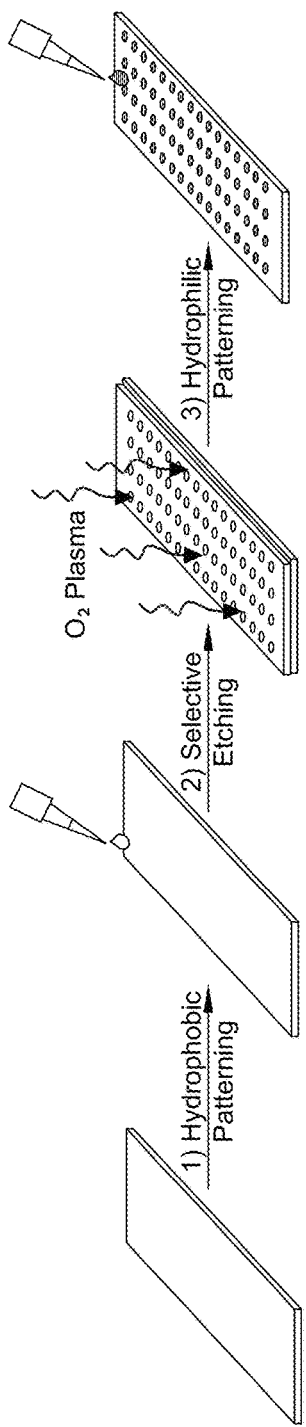
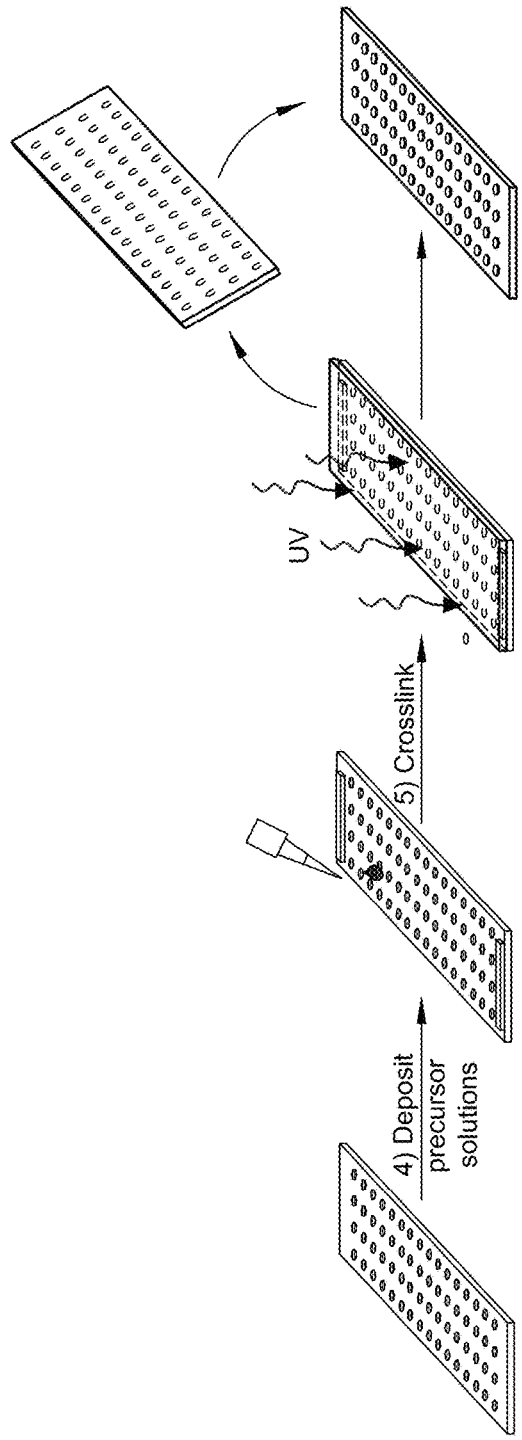
FIG. 1A
FIG. 1B

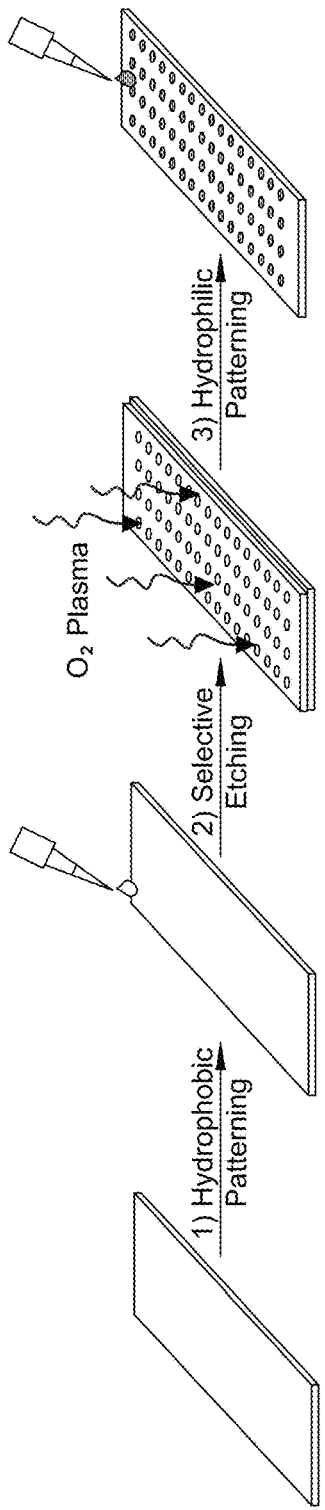
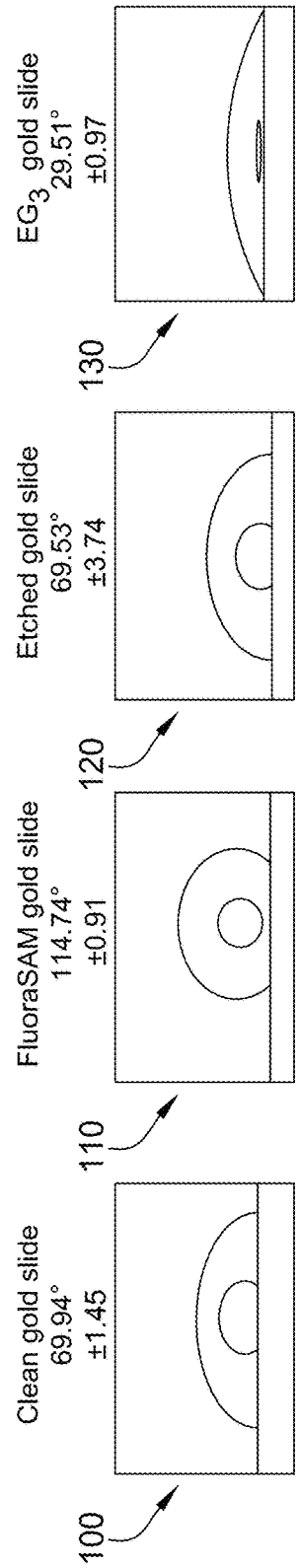
FIG. 2A
FIG. 2B

SEQUENCE LISTING

```
<160> NUMBER OF SEQ ID NOS: 37

<210> SEQ ID NO 1
<211> LENGTH: 4
<212> TYPE: PRT
<213> ORGANISM: Artificial Sequence
<220> FEATURE:
<223> OTHER INFORMATION: Synthetic

<400> SEQUENCE: 1

Arg Gly Asp Ser
1

<210> SEQ ID NO 2
<211> LENGTH: 5
<212> TYPE: PRT
<213> ORGANISM: Artificial Sequence
<220> FEATURE:
<223> OTHER INFORMATION: Synthetic

<400> SEQUENCE: 2

Cys Arg Gly Asp Ser
1               5
```

```
<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Gly Arg Gly Asp Ser Pro
1               5

<210> SEQ ID NO 4
<211> LENGTH: 22
<212> TYPE: PRT
<213> ORGANISM: Artificial Sequence
<220> FEATURE:
<223> OTHER INFORMATION: Synthetic

<400> SEQUENCE: 4

Cys Arg Gly Asp Gly Gly Gly Gly Gly Gly Gly Gly Gly Gly Gly Gly
1               5                   10                  15

Gly Pro His Ser Arg Asn
            20

<210> SEQ ID NO 5
<211> LENGTH: 19
<212> TYPE: PRT
<213> ORGANISM: Artificial Sequence
<220> FEATURE:
<223> OTHER INFORMATION: Synthetic

<400> SEQUENCE: 5

Cys Arg Gly Asp Ser Gly Ser Gly Ser Gly Ser Gly Ser Gly Pro His
1               5                   10                  15

Ser Arg Asn

<210> SEQ ID NO 6
<211> LENGTH: 6
<212> TYPE: PRT
<213> ORGANISM: Artificial Sequence
<220> FEATURE:
<223> OTHER INFORMATION: Synthetic

<400> SEQUENCE: 6

Cys Arg Gly Asp Ser Pro
1               5

<210> SEQ ID NO 7
<211> LENGTH: 10
<212> TYPE: PRT
<213> ORGANISM: Artificial Sequence
<220> FEATURE:
<223> OTHER INFORMATION: Synthetic

<400> SEQUENCE: 7

Gly Cys Tyr Gly Arg Gly Asp Ser Pro Gly
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8
```

```
Arg Gly Asp Phe Cys
1               5

<210> SEQ ID NO 9
<211> LENGTH: 4
<212> TYPE: PRT
<213> ORGANISM: Artificial Sequence
<220> FEATURE:
<223> OTHER INFORMATION: Synthetic

<400> SEQUENCE: 9

Arg Asp Gly Ser
1

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Cys Arg Asp Gly Ser
1               5

<210> SEQ ID NO 11
<211> LENGTH: 10
<212> TYPE: PRT
<213> ORGANISM: Artificial Sequence
<220> FEATURE:
<223> OTHER INFORMATION: Synthetic

<400> SEQUENCE: 11

Gly Cys Tyr Gly Arg Gly Asp Ser Pro Gly
1               5                   10

<210> SEQ ID NO 12
<211> LENGTH: 5
<212> TYPE: PRT
<213> ORGANISM: Artificial Sequence
<220> FEATURE:
<223> OTHER INFORMATION: Synthetic

<400> SEQUENCE: 12

Pro His Ser Arg Asn
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic

<400> SEQUENCE: 13

Gly Trp Gly Gly Arg Gly Asp Ser Pro
1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic

<400> SEQUENCE: 14

Ser Ile Asp Gln Val Glu Pro Tyr Ser Ser Thr Ala Gln
```

<210> SEQ ID NO 15
<211> LENGTH: 11
<212> TYPE: PRT
<213> ORGANISM: Artificial Sequence
<220> FEATURE:
<223> OTHER INFORMATION: Synthetic

<400> SEQUENCE: 15

Gly Arg Asn Ile Ala Glu Ile Ile Lys Asp Ile
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Asp Ile Thr Tyr Val Arg Leu Lys Phe
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Asp Ile Thr Val Thr Leu Asn Arg Leu
1               5

<210> SEQ ID NO 18
<211> LENGTH: 8
<212> TYPE: PRT
<213> ORGANISM: Artificial Sequence
<220> FEATURE:
<223> OTHER INFORMATION: Synthetic

<400> SEQUENCE: 18

Gly Arg Tyr Val Val Leu Pro Arg
1               5

<210> SEQ ID NO 19
<211> LENGTH: 13
<212> TYPE: PRT
<213> ORGANISM: Artificial Sequence
<220> FEATURE:
<223> OTHER INFORMATION: Synthetic

<400> SEQUENCE: 19

Gly Asn Arg Trp His Ser Ile Tyr Ile Thr Arg Phe Gly
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Synthetic

<400> SEQUENCE: 20

Gly Ala Ser Ile Lys Val Ala Val Ser Ala Asp Arg
1               5                   10

```
<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Gly Thr Thr Val Lys Tyr Ile Phe Arg
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Gly Ser Ile Lys Ile Arg Gly Thr Tyr Ser
1               5                   10

<210> SEQ ID NO 23
<211> LENGTH: 7
<212> TYPE: PRT
<213> ORGANISM: Artificial Sequence
<220> FEATURE:
<223> OTHER INFORMATION: Synthetic

<400> SEQUENCE: 23

Gly Ser Ile Asn Asn Asn Arg
1               5

<210> SEQ ID NO 24
<211> LENGTH: 9
<212> TYPE: PRT
<213> ORGANISM: Artificial Sequence
<220> FEATURE:
<223> OTHER INFORMATION: Synthetic

<400> SEQUENCE: 24

Ser Asp Pro Gly Tyr Ile Gly Ser Arg
1               5

<210> SEQ ID NO 25
<211> LENGTH: 5
<212> TYPE: PRT
<213> ORGANISM: Artificial Sequence
<220> FEATURE:
<223> OTHER INFORMATION: Synthetic

<400> SEQUENCE: 25

Tyr Ile Gly Ser Arg
1               5

<210> SEQ ID NO 26
<211> LENGTH: 14
<212> TYPE: PRT
<213> ORGANISM: Artificial Sequence
<220> FEATURE:
<223> OTHER INFORMATION: Synthetic

<400> SEQUENCE: 26

Gly Thr Pro Gly Pro Gln Gly Ile Ala Gly Gln Gly Val Val
1               5                   10
```

<210> SEQ ID NO 27
<211> LENGTH: 14
<212> TYPE: PRT
<213> ORGANISM: Artificial Sequence
<220> FEATURE:
<223> OTHER INFORMATION: Synthetic

<400> SEQUENCE: 27

Gly Thr Pro Gly Pro Gln Gly Ile Ala Gly Gln Arg Val Val
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Synthetic

<400> SEQUENCE: 28

Met Asn Tyr Tyr Ser Asn Ser
1               5

<210> SEQ ID NO 29
<211> LENGTH: 12
<212> TYPE: PRT
<213> ORGANISM: Artificial Sequence
<220> FEATURE:
<223> OTHER INFORMATION: Synthetic

<400> SEQUENCE: 29

Lys Lys Gln Arg Phe Arg His Arg Asn Arg Lys Gly
1               5                   10

<210> SEQ ID NO 30
<211> LENGTH: 18
<212> TYPE: PRT
<213> ORGANISM: Artificial Sequence
<220> FEATURE:
<223> OTHER INFORMATION: Synthetic

<400> SEQUENCE: 30

Gly Gly Gly Lys Leu Thr Trp Gln Glu Leu Tyr Gln Leu Lys Tyr Lys
1               5                   10                  15

Gly Ile

<210> SEQ ID NO 31
<211> LENGTH: 15
<212> TYPE: PRT
<213> ORGANISM: Artificial Sequence
<220> FEATURE:
<223> OTHER INFORMATION: Synthetic

<400> SEQUENCE: 31

Lys Leu Thr Trp Gln Glu Leu Tyr Gln Leu Lys Tyr Lys Gly Ile
1               5                   10                  15

<210> SEQ ID NO 32
<211> LENGTH: 12
<212> TYPE: PRT
<213> ORGANISM: Artificial Sequence
<220> FEATURE:
<223> OTHER INFORMATION: Synthetic

<400> SEQUENCE: 32

Lys Ile Pro Lys Ala Ser Ser Val Pro Thr Glu Leu
1               5                   10

<210> SEQ ID NO 33
<211> LENGTH: 20
<212> TYPE: PRT
<213> ORGANISM: Artificial Sequence
<220> FEATURE:
<223> OTHER INFORMATION: Artificial

<400> SEQUENCE: 33

Lys Ile Pro Lys Ala Ser Ser Val Pro Thr Glu Leu Ser Ala Ile Ser
1               5                   10                  15

Thr Leu Tyr Leu
            20

<210> SEQ ID NO 34
<211> LENGTH: 8
<212> TYPE: PRT
<213> ORGANISM: Artificial Sequence
<220> FEATURE:
<223> OTHER INFORMATION: Synthetic

<400> SEQUENCE: 34

Lys Arg Thr Gly Gln Tyr Lys Leu
1               5

<210> SEQ ID NO 35
<211> LENGTH: 14
<212> TYPE: PRT
<213> ORGANISM: Artificial Sequence
<220> FEATURE:
<223> OTHER INFORMATION: Synthetic

<400> SEQUENCE: 35

Lys Cys Gly Gly Pro Gln Gly Ile Trp Gly Gln Gly Cys Lys
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic

<400> SEQUENCE: 36

Lys Cys Gly Gly Pro Gln Gly Ile Ala Gly Gln Gly Cys Lys
1               5                   10

<210> SEQ ID NO 37
<211> LENGTH: 17
<212> TYPE: PRT
<213> ORGANISM: Artificial Sequence
<220> FEATURE:
<223> OTHER INFORMATION: Synthetic

<400> SEQUENCE: 37

Cys Lys Asp Ala Pro Tyr Glu Trp Asn Phe Asp Ile Leu Tyr Ala Phe
1               5                   10                  15

Glu

METHOD FOR FORMING HYDROGEL ARRAYS USING SURFACES WITH DIFFERENTIAL WETTABILITY

CROSS-REFERENCE TO RELATED APPLICATIONS

This application claims priority to U.S. patent application Ser. No. 61/978,032, filed on Apr. 10, 2014, the disclosure of which is hereby expressly incorporated by reference in its entirety.

STATEMENT REGARDING FEDERALLY SPONSORED RESEARCH OR DEVELOPMENT

This invention was made with government support under HL093282 and EB 016381 awarded by the National Institutes of Health. The government has certain rights in the invention.

STATEMENT IN SUPPORT FOR FILING A SEQUENCE LISTING

A paper copy of the Sequence Listing and a computer readable form of the Sequence Listing containing the file named "P140097US01 (28243-185)_ST25.txt", which is 7704 bytes in size (as measured in MICROSOFT WINDOWS® EXPLORER), are provided herein and are herein incorporated by reference. This Sequence Listing consists of SEQ ID NOs:1-37.

BACKGROUND OF THE DISCLOSURE

The present disclosure relates generally to methods for preparing biomaterial arrays and methods for using the biomaterial arrays. More particularly, the present disclosure relates to hydrogel arrays, methods for preparing hydrogel arrays and methods for screening cell-substrate interactions using the hydrogel arrays.

The development of most tissue types involves a complex interplay of multiple signals leading to controlled precursor cell differentiation into mature, tissue-specific cell types. For example, mesenchymal stem cells (MSCs) may be differentiated in vitro into osteoblasts, chondrocytes, myoblasts, adipocytes, neurons, and endothelial cells by exposure to a variety of growth factors. Exposure to growth factors may be controlled by the media and the substrates upon which the cells are cultured. Substantial progress has been made in the development of defined media, but only more recently has the role of substrates and cell-substrate adhesion on cell growth been examined.

Based on studies to determine defined media, it has become apparent that the substrate is important for successful cellular growth and tissue generation. For example, it has been demonstrated that attachment to the substrate by human embryonic stem cells may contribute to the variability in whether the cells remain undifferentiated or undergo differentiation. Therefore, it is important to not only identify cell culture media for successful cell culture conditions, but to also identify defined substrates.

Screening well-defined surfaces in an array format allows rapid identification of specific molecules that promote cellular adhesion, cellular spreading, proliferation, migration and differentiation, as well as molecules that regulate cell behavior. Biomaterial arrays such as self-assembled monolayers ("SAMs") in array formats (i.e., SAM arrays) have been constructed that present ligands to cells plated onto the array. A SAM is an organized layer of amphiphilic molecules in which one end of the molecule exhibits a specific, reversible affinity for a substrate and the other end of the molecule has a functional group. Because the molecule used to form the SAM array is polarized, the hydrophilic "head groups" assemble together on the substrate, while the hydrophobic tail groups assemble far from the substrate. Areas of close-packed molecules nucleate and grow until the surface of the substrate is covered in a single monolayer.

The use of alkanethiols to construct SAM arrays allow for the formation of reproducible SAM arrays and surfaces. SAM arrays may be used to identify specific ligands or epitopes that promote cellular attachment, spreading, proliferation, migration and differentiation. Additionally, SAM arrays may be patterned such that ligands will be presented to the cells in defined areas of the array.

While chemically-defined SAM array approaches have provided unique insights into several biological processes, SAM arrays have yet to become a commonly used tool for biology. One potential reason for their lack of use is that SAM array fabrication can be labor intensive. In typical experiments investigating SAM arrays presenting a range of different ligands or ligand densities, each condition and replicate requires an individual gold substrate. In most approaches, substrates are manually handled before and after each step of an experiment that can include gold substrate cleaning, SAM array formation, ligand conjugation, cell seeding, and analysis. Performing a SAM array-based experiment comparable to a standard 96-well plate may require close to 1000 handling steps before performing any type of analysis.

Biomaterial array patterning approaches have been developed to spatially localize ligands to create spatially and chemically-defined cell culture substrates. Microcontact printing, for example, generates patterned SAM arrays by "inking" alkanethiolate molecules onto a flexible elastomeric stamp and stamping the alkanethiolates onto a gold surface, which transfers a pattern of ligands onto the gold substrate. The remaining areas of bare gold are then "backfilled" with a second alkanethiolate species to generate a bio-inert SAM surrounding the stamped hydrophobic alkanethiolate domains. The substrates are then bathed in a solution of ligands that spontaneously adsorb to the hydrophobic alkanethiolate regions to create patterned islands for cell attachment. Microfluidics approaches for SAM array patterning typically use elastomeric stamps with microscale features that form channels when passively adhered to a SAM. Localized ligand conjugation can then be achieved by flowing reaction solutions through the channels exposing them to reactive terminal moieties presented by the underlying SAM. Photochemistry in combination with micropatterned photomasks can be used to create patterned SAM arrays by selectively protecting a reactive terminal moiety and then selectively deprotecting the terminal moiety to locally immobilize ligands on the SAM. SAM array patterning can also be accomplished by locally destroying/removing regions of a fully formed SAM, then reforming new SAMs in the destroyed regions.

While biomaterial arrays such as SAM arrays provide an excellent model substrate for investigating the effects of an immobilized ligand on cell behavior, preparing SAM array platforms using less labor intensive processes are needed to make SAM array use more widespread. Accordingly, there exists a need for alternative methods for preparing patterned biomaterial arrays to identify surfaces that will support survival and growth of cells in culture, allow rapid identification of specific molecules that promote cellular adhesion, cellular spreading, proliferation, migration, differentiation and regulate cellular behavior.

BRIEF DESCRIPTION OF THE DISCLOSURE

The present disclosure relates generally to methods for preparing biomaterial arrays and methods for using the biomaterial arrays. More particularly, the present disclosure relates to hydrogel arrays, methods for preparing hydrogel arrays and methods for screening molecule-molecule interactions using the hydrogel arrays.

In accordance with the present disclosure, methods for preparing patterned hydrogel arrays to identify surfaces that will support survival and growth of cells in culture, allow rapid identification of specific molecules that promote cellular adhesion, cellular spreading, proliferation, migration, differentiation and regulate cellular behavior have been discovered. The hydrogel arrays of the present disclosure can also be used for two-dimensional (2D) and three-dimensional (3D) cell culture. The hydrogel arrays of the present disclosure can further be used for two-dimensional enrichment of biomolecules such as, for example, biomolecules, to cell surfaces using soluble factor binding peptides. The hydrogel arrays of the present disclosure can also be used as sources for soluble factors by encapsulating cells and soluble-factor releasing microparticles, which can be used to promote angiogenesis, promote tubulogenesis, promote morphogenic processes and screening for drug toxicity, for example. Additionally, the hydrogel arrays of the present disclosure can be used to analyze molecule-molecule interactions such as, for example, ligand-target interactions, antibody-antigen interactions, protein-protein interactions, growth factor-binding ligand interactions, receptor-ligand interactions and the like. Use of the hydrogel arrays of the present disclosure to analyze molecule-molecule interactions can allow for determining specificity of binding, affinity of binding and the like.

In one aspect, the present disclosure is directed to a method for preparing a patterned hydrogel array. The method includes contacting a hydrogel precursor solution with a patterned substrate, wherein the patterned substrate includes a hydrophobic region and a hydrophilic region; placing a surface-modified substrate onto the hydrogel precursor solution such that the hydrogel precursor solution is located between the patterned substrate and the surface-modified substrate; polymerizing the hydrogel precursor solution; and separating the surface-modified substrate from the patterned substrate to result in the patterned hydrogel array. In particularly suitable embodiments, the hydrogel precursor solution comprises a polymer and a multifunctional polymer crosslinker.

In another aspect, the present disclosure is directed to a patterned hydrogel array. In one embodiment, the patterned hydrogel array is prepared using the method generally described herein.

In yet another aspect, the present disclosure is directed to a method for screening molecule-molecule interactions. The method includes preparing a patterned hydrogel array, wherein the patterned hydrogel array includes at least one ligand; contacting the hydrogel array with a molecule known to or suspected of interacting with the at least one ligand; and analyzing the hydrogel array. The patterned hydrogel array can be prepared by contacting a hydrogel precursor solution with a patterned substrate, wherein the patterned substrate includes a hydrophobic region and a hydrophilic region; placing a surface-modified substrate onto the hydrogel precursor solution; polymerizing the hydrogel precursor solution; and separating the surface-modified substrate from the patterned substrate to result in the patterned hydrogel array. In particularly suitable embodiments, the hydrogel precursor solution includes a polymer and a multifunctional polymer crosslinker.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIGS. 1A-1B are schematic illustrations of the steps for preparing a hydrogel array of the present disclosure.

FIG. 2A is a schematic illustration of the steps for patterning a metal-coated substrate used in the method for preparing a hydrogel array of the present disclosure.

FIG. 2B are end view drawings of the metal-coated substrate during the steps for patterning a metal-coated substrate shown in FIG. 2A.

Figure 3:
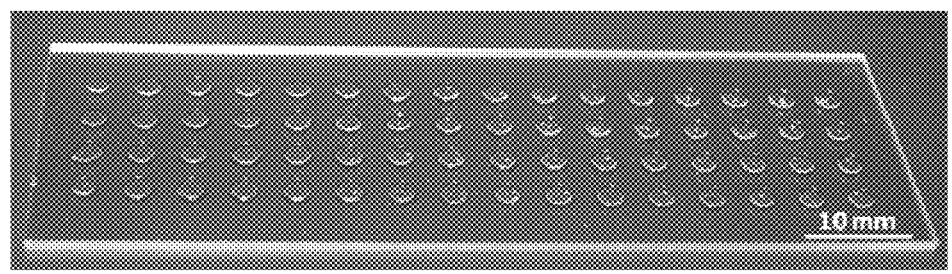
FIG. 3 is a photograph of a hydrogel array with 64 individual hydrogel spots prepared using the methods of the present disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION OF THE DISCLOSURE

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

In accordance with the present disclosure, methods for preparing biomaterial arrays for screening molecule-molecule interactions have been discovered. More particularly, the present disclosure relates to hydrogel arrays. In one aspect, hydrogel arrays can be prepared with controlled hydrogel modulus, hydrogel polymer density, hydrogel crosslinker density, hydrogel ligand identity and hydrogel ligand density and to methods for preparing the hydrogel arrays. It has been found that the hydrogel arrays with controlled hydrogel modulus, hydrogel polymer density, hydrogel crosslinker density, hydrogel ligand identity and hydrogel ligand density offer an improved screening method for molecule-molecule interactions. The hydrogel arrays of the present disclosure can be functionalized with biomolecules, are compatible with cell culture and are biocompatible such that the hydrogel arrays can be implanted into animals including, for example, humans. The hydrogel arrays of the present disclosure can also be used to alter (e.g., enhance, inhibit and change) cell function such as, for example, cell proliferation, cell differentiation, cell self-renewal, cell spreading, cell attachment, cell-cell contact, cell contractility, cell migration, tissue formation and self-organization of cells to form cell-cell contacts and organization leading to tissue formation. Hydrogel arrays can also be prepared to include regions that are surrounded by hydrogel to form regions that are free (or devoid) of hydrogel (referred to herein as "hydrogel-free pools"). Hydrogel arrays having hydrogel pools can be used as described above to be functionalized with biomolecules, are compatible with cell culture and are biocompatible such that the hydrogel arrays can be implanted into animals including, for example, humans. Hydrogel arrays having hydrogel pools can also be used to alter (e.g., enhance, inhibit and change) cell function such as, for example, cell proliferation, cell differentiation, cell self-renewal, cell spreading, cell attachment, cell-cell contact, cell contractility, cell migration, tissue formation and self-organization of cells to form cell-cell contacts and organization leading to tissue formation. Hydrogel arrays having hydrogel pools can be used to culture different cell types in each of the pools and add different components to each of the pools. In hydrogel arrays composed of pools, the walls of the pools can serve as the physical barrier against the mixing of the components in neighboring pools.

As known by those skilled in the art, a hydrogel is a network of polymer chains that are hydrophilic in which a polymeric material and water are in an equilibrated form. The hydrogel is formed using unpolymerized starting components. The polymeric material can be, for example, a natural polymer material, a synthetic polymer material and combinations thereof.

The methods for preparing hydrogel arrays of the present disclosure using thiol-ene polymerization to form hydrogels advantageously allows for the direct incorporation of peptides into the hydrogel network during polymerization by including a cysteine in the amino acid sequence during synthesis, which allows for eliminating the need for post-synthetic modifications. In this way, peptides can be utilized as crosslinkers by including cysteine on each end or they can be incorporated as pendant groups, which can be pre-coupled to the polymer backbone and mixed in varying combinations or incorporated during polymerization for simplicity.

Methods for Preparing Patterned Hydrogel Arrays

In one aspect, the present disclosure is directed to a method for preparing a patterned hydrogel array. The method includes contacting a hydrogel precursor solution with a patterned substrate, wherein the patterned substrate includes a hydrophobic region and a hydrophilic region; placing a surface-modified substrate onto the hydrogel precursor solution such that the hydrogel precursor solution is located between the patterned substrate and the surface-modified substrate; polymerizing the hydrogel precursor solution; and separating the surface-modified substrate from the patterned substrate, to result in the patterned hydrogel array. (See, FIG. 1A-1B). Thus, the polymer hydrogel precursor solution polymerizes between the patterned substrate and the surface-modified substrate and the resultant hydrogel transfers with the surface-modified substrate such that the surface-modified substrate includes the patterned hydrogel array. In one embodiment, the patterned hydrogel array can be patterned to include an array of hydrogel spots surrounded by a hydrogel-free background as described in more detail below. In another embodiment, the patterned hydrogel array can be patterned such that an array of hydrogel-free spots (or pools) are formed within a hydrogel background as described in more detail below.

Figure 5:
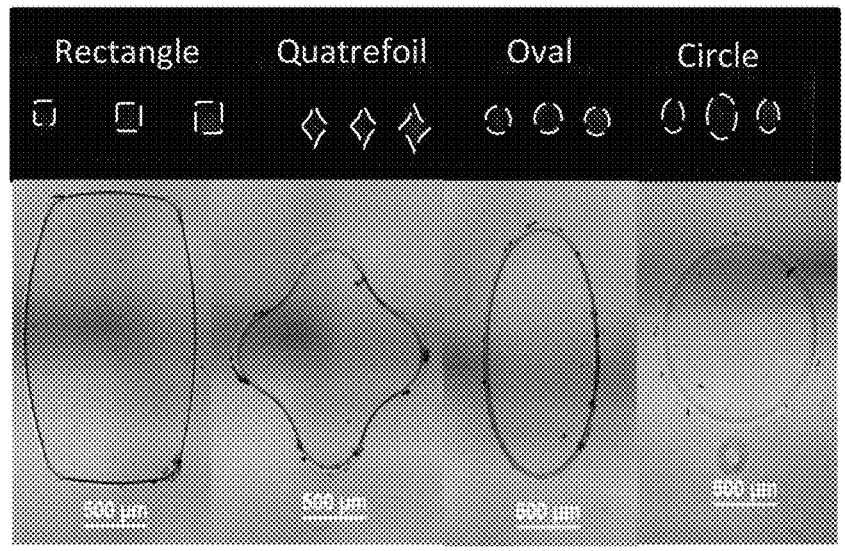
FIG. 5 illustrates high magnification top-view images showing different shapes of individual hydrogel spots.

In patterned hydrogel arrays having hydrogel spots, the resultant hydrogel array can be patterned to result in differential wettability to define the geometry of each hydrogel spot and confine the contents of each hydrogel spot of the array, as well as define the spatial pattern of each hydrogel spot in the array in relation to neighboring spots. This is particularly useful for preparing hydrogel arrays for use with common microarray add-ons of different sizes and dimensions consistent with those of common multi-well plates (e.g., 96 well plates, 384 well plates, etc.) This is also useful for use with multichannel pipettes for enhanced-throughput cell culture, media exchange, and the like. The individual hydrogel spots of the array can have any desired shape (see e.g., FIG. 5). For example, the shape can be circular, round, oval, quatrefoil, rectangular, triangular, star-shaped, diamond-shaped, combinations thereof, and the like. Patterns of hydrogel spots may also be created in rows, spirals, circles, squares, rectangles, combinations thereof, and the like. The shape of the individual hydrogel spot can be varied by changing the pattern of the stencil used for etching during patterning of the patterned substrate.

In patterned hydrogel arrays having hydrogel-free spots, the individual hydrogel-free spots can have any desired shape. For example, the shape can be circular, round, oval, quatrefoil, rectangular, triangular, star-shaped, diamond-shaped, combinations thereof, and the like. Patterns of hydrogel-free spots may also be created in rows, spirals, circles, squares, rectangles, combinations thereof, and the like. The shape of the individual hydrogel-free spot can be varied by changing the pattern of the stencil used for etching during patterning of the patterned substrate.

The upper size limit of the hydrogel array depends on the dimensions of the patterned substrate and/or the dimensions of the surface-modified substrate. The resultant hydrogel array can also be patterned to result in individual hydrogel spots and hydrogel-free spots having any desired sizes. The size and shape of the individual hydrogel spot and hydrogel-free spot can be varied by changing the pattern of the stencil used for etching during patterning of the patterned substrate. Suitable individual hydrogel spot size of the hydrogel array can be small enough to accommodate a single cell, but also large enough to accommodate many cells, for example. Thus, the individual hydrogel spot size of the hydrogel array can have any desired diameter. Particularly suitable individual hydrogel spot sizes of the hydrogel array can be about 10 μm and larger.

A patterned substrate can be prepared by creating hydrophobic regions and hydrophilic regions formed by self-assembled monolayers (SAMs). Suitable substrates for forming self-assembled monolayers are known to those skilled in the art and can be, for example, metal-coated substrates, silicon substrates, diamond substrates, glass substrates, quartz substrates, activated aluminum substrates, copper substrates and the like (as described in Love et al., Chem. Rev. 2005, 105:1103-1169, for example, which is hereby incorporated by reference to the extent its disclosure is consistent with the present disclosure).

In one embodiment, the patterned substrate can be, for example, a patterned metal-coated substrate. Suitable metals for preparing the patterned metal-coated substrates can be, for example, gold, titanium, copper, stainless steel, silver, platinum, ruthenium, rhodium, palladium, osmium, iridium, iron, silicon, aluminum, nickel, mica, cadmium, gallium, germanium, mercury, indium, lead, zinc, cobalt, hafnium and combinations thereof. Using the metal substrates above has an advantage as the metal and alkanethiols have a strong affinity, and thus, form stable bonds.

Suitable metal-coated substrates are known to those skilled in the art and can be, for example, metal-coated glass, metal-coated silicon, metal-coated mica and metal-coated plastics. A particularly suitable metal-coated substrate is a gold-coated glass slide. The metal-coated substrate can further include a metal adhesion layer. Metal adhesion layers (also referred to in the art as a primer layer) are known by those skilled in the art to provide stability and improve the adhesion of metals that do not form oxides readily to substrates with an oxidized surface. The metal adhesion layer can be, for example, a titanium adhesion layer, a gold adhesion layer, a chromium adhesion layer, a nickel adhesion layer and other suitable metal adhesion layers known to those skilled in the art. A particularly suitable metal-coated substrate can be a gold-coated glass slide further including a titanium adhesion layer (commercially available from Evaporated Metal Films, Ithica, N.Y.). Alternatively, a substrate can be coated with a metal using methods known to those skilled in the art such as, for example, evaporation, vapor deposition, electrodeposition, and electroless deposition.

The patterned metal-coated substrate can be prepared, for example, by forming regions with differential wettability on a substrate by immersing the substrate in a perfluorinated alkanethiol solution to allow perfluorinated alkanethiolate self-assembled monolayers (fluoraSAMs) to form. To form hydrophilic regions, a stencil can be placed on the fluoraSAMs metal-coated substrate to selectively protect regions of the fluoraSAMs metal-coated substrate from plasma etching. Exposed regions of the fluoraSAMs substrate can then be etched by oxygen plasma treatment to form etched fluoraSAMs in the substrate. The substrate is then immersed in a hydroxyl-terminated alkanethiol solution to form a hydrophilic alkanethiolate SAM ($EG_3SAM$) in the etched regions of the substrate. The resulting patterned substrate possesses differential wettability based on the hydrophobic SAMs and hydrophilic SAMs.

In another embodiment, the patterned substrate can be, for example, a patterned silicon substrate. The patterned silicon substrate can be prepared using silicon chemistry, for example (as described in Strother et al., J. Am. Chem. Soc. 2000, 122:1205-1209, which is hereby incorporated by reference to the extent its disclosure is consistent with the present disclosure). The silicon surface can be prepared by reacting a hydrogen-terminated Si(111) surface with an ω-alkene such as, for example, ω-undecylenic acid methyl and trifluoroethyl ester, to create a hydrophobic layer on the silicon, which can then be etched using an oxygen plasma treatment or a chemical treatment to form hydrophilic regions using the patterning techniques described herein. Also, hydrogen-terminated Si(001) surfaces, especially etched to create porous Si can be used to prepare a patterned silicon substrate. Hydrogen terminated porous silicon can be modified using "hydrosilylation" chemistry, which is the thermal attachment of C=C containing molecules to the H-terminated silicon surface. The C=C containing molecule can include any functional group on the other end of the molecule including, for example, fluorinated compounds, a carboxylic acid (or a protected carboxylic acid), alkane chains, and the like. When using a molecule containing a carboxylic acid group, further modification is possible to change the hydrophobicity, such as through the use of carbodiimide chemistry to link an amine-containing molecule (see e.g., Schwartz et al., 2005 Phys. Stat. Sol. (a) 202(8):1380-1384, which is hereby incorporated by reference to the extent its disclosure is consistent with the present disclosure).

In another embodiment, the patterned substrate can be, for example, a patterned diamond substrate. The patterned diamond substrate can be prepared as described in Strother et al. (Langmuir, 2002, 18:968-971, which is hereby incorporated by reference to the extent its disclosure is consistent with the present disclosure). Hydrogel arrays can then be prepared as described herein using the patterned diamond substrates. Notably, diamond surfaces are naturally hydrophobic and provide the added benefits of direct use, as well as indefinite re-use as the patterned substrate when coupled with post-treatments to remove the hydrogel.

In another embodiment, the patterned substrate can be a polydimethylsiloxane (PDMS) substrate. PDMS is a hydrophobic, silicon-based organic polymer. Plasma treatment of exposed PDMS regions can selectively confer hydrophilic properties to the exposed PDMS regions. Hydrogel arrays can then be prepared as described herein using PDMS substrates having hydrophilic properties. Notably, PDMS surfaces are naturally hydrophobic and provide the added benefits of direct use, as well as indefinite re-use as the patterned substrate when coupled with post-treatments to remove the hydrogel.

Figure 4:
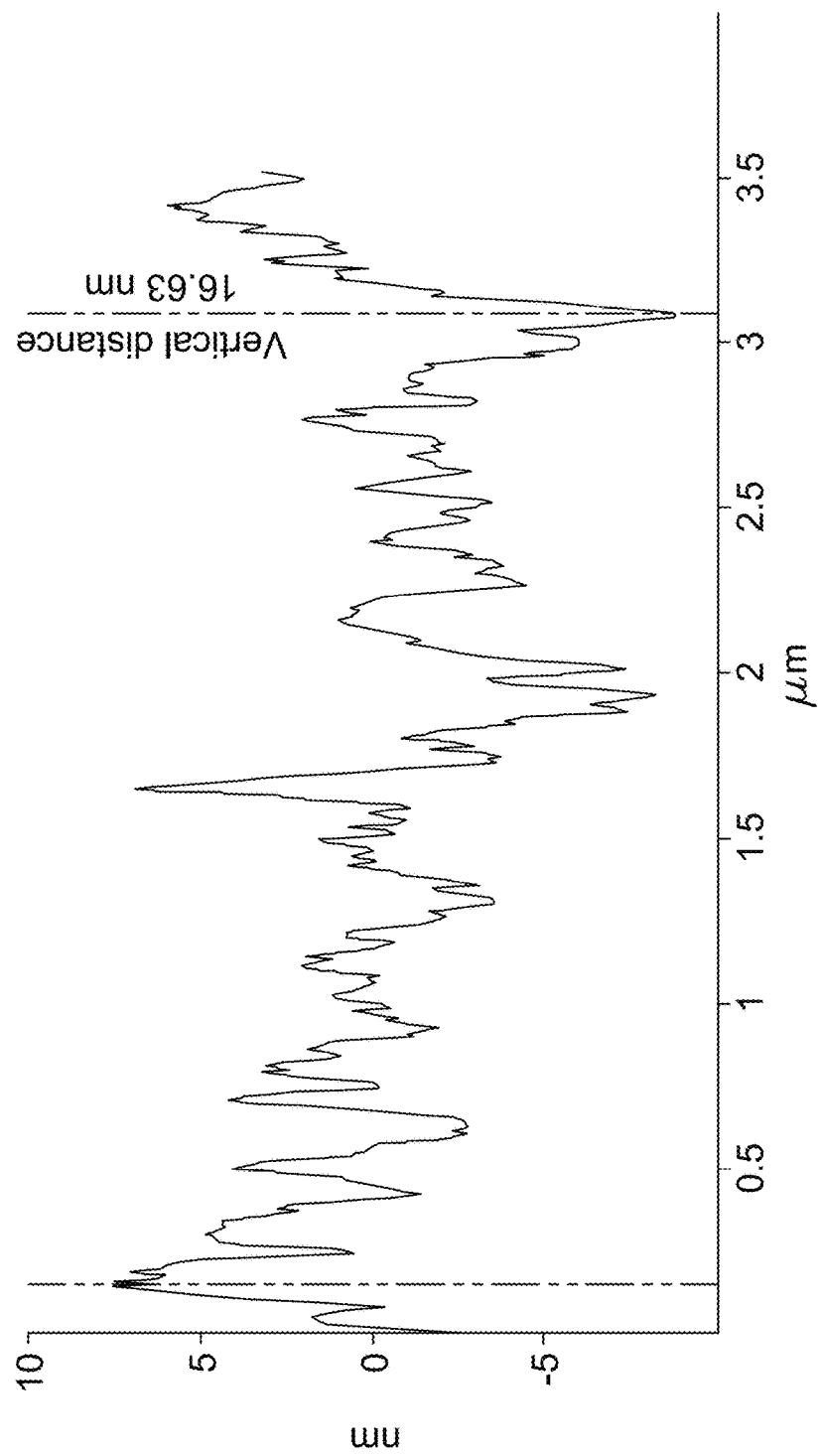
FIG. 4 is a graph illustrating the surface roughness of a hydrogel array as determined by atomic force microscopy.
Figure 6:
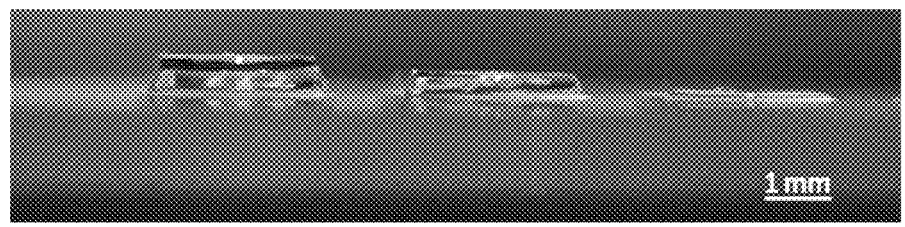
FIG. 6 is a side-on image showing individual hydrogel spots having different heights.

The method can further include placing a spacer between the patterned substrate and the surface-modified substrate. The spacer placed onto the patterned substrate while performing the method functions to define the height (or thickness) of the hydrogel forming the hydrogel array. A spacer may be particularly desirable when preparing higher (i.e., thicker) hydrogel arrays. Thus, the hydrogel array can have any desirable height (see e.g., FIG. 6). Suitable heights of the hydrogel array can be from about 20 micrometers (µm) to about 1 millimeter, however, hydrogel arrays can be made much higher than 1 millimeter if desired. The spacer also functions to prevent direct contact between the surface of the patterned substrate and the surface-modified substrate during formation of the hydrogel. The spacer used in the method can be any suitable material known to those skilled in the art. A particularly suitable spacer can be, for example, polydimethylsiloxane (PDMS). The height the hydrogel array can be determined, for example, using a microscope to focus from the top of the hydrogel down to the substrate, using a microscope to focus from the substrate up to the top of the hydrogel, and by measuring the surface roughness of a hydrogel array as determined by atomic force microscopy (see e.g., FIG. 4).

The method further includes contacting a hydrogel precursor solution with the patterned substrate. In particular, the hydrogel precursor solution is contacted with the hydrophilic regions of the patterned substrate. The hydrophobic regions of the patterned substrate serve as a barrier between neighboring hydrophilic regions and also allow for the isolation of each hydrophilic region. The hydrogel precursor solution can be, for example, a combination of a polymer and a multifunctional polymer crosslinker.

Suitable polymers for the hydrogel precursor solution are known by those skilled in the art and can include, for example, poly(ethylene glycol), hyaluronic acid, gelatin, collagen, MATRIGEL®, dithiol polymers (e.g., acrylamide), click-based composite hydrogels (as discussed in Polizzotti et al. Biomacromolecules 2008, 9:1084-1087, which is hereby incorporated by reference to the extent its disclosure is consistent with the present disclosure), poly(ethylene glycol)-diacrylate, poly(ethylene glycol)-vinyl sulfone, and the like. Particularly suitable polymers can be, for example, poly(ethylene glycol), thiolated hyaluronic acid, thiolated gelatin, collagen, and the like. Particularly suitable polymers can also be, for example, functionalized polymers. Functionalization of the polymer can be confirmed with $^1$H nuclear magnetic resonance spectroscopy, mass spectroscopy, Elman's reagent, UV-Vis spectroscopy, infrared spectroscopy, and other methods known to those skilled in the art, for example.

A particularly suitable functionalized polymer can be, for example, eight-arm poly(ethylene glycol) with terminal hydroxyl (—OH) groups (commercially available from JenKem Technology USA, Allen, Tex. and Laysan Bio, Inc., Arab, Ala.) that is functionalized with norbornene. Eight-arm poly(ethylene glycol) can be functionalized with norbornene as described in Fairbanks et al. (Adv. Mater. 2009, 21:5005-5010).

Other particularly suitable polymers are poly(ethylene glycols) that may be functionalized using click chemistry. "Click" chemistry is an extremely versatile method for chemically attaching biomolecules, which is used to describe the [3+2] cycloaddition between alkyne and azide functional groups. Azides and alkynes are largely inert towards biological molecules and aqueous environments, which allows the use of the Huisgen 1,3-dipolar cycloaddition to yield stable triazoles that are very difficult to oxidize or reduce. Both the copper(I)-catalyzed and copper-free strained-alkyne variant reactions are mild and very efficient. These reactions can also be performed in small volumes of aqueous solutions, are insensitive to oxygen and water, and robust to functional groups on peptides (4, 5). Click chemistry allows for selectivity in conjugation reactions in biological samples such as, for example, oligonucleotides and proteins. Particularly suitable reagents for click chemistry are commercially available from Laysan Bio Inc. (Arab, Ala.).

Suitable multifunctional polymer crosslinkers for use in the hydrogel precursor solution are known by those skilled in the art. In particular, the multifunctional crosslinker can be, for example, a bifunctional polymer crosslinker and a multifunctional polymer crosslinker (n>=2) and terminated with a functional group that can form a covalent bond with the polymer of the hydrogel precursor solution. Particularly suitable bi-functional polymer crosslinkers and multifunctional polymer crosslinkers can be, for example, polyethylene glycol dithiol (PEG-DT), protease-degradable crosslinkers and multi-arm poly(ethylene glycol) terminated with thiol (e.g., 4-arm PEG terminated with thiol). Alternative functional crosslinkers can be acrylate-functionalized crosslinkers such as, for example, PEG-diacrylate, PEG-dimethacrylate and the like (commercially available from Poly-Sciences, Inc., Warrington, Pa.). Suitable protease-degradable crosslinkers can be, for example, matrix metalloproteinase-degradable crosslinkers as described in Nagase and Fields (Biopolymers 1996, 40:399-416, which is hereby incorporated by reference to the extent it is consistent with the present disclosure). Alternatively, the polymer crosslinker can be, for example a streptavidin-terminated polymer crosslinker and biotin-terminated polymer crosslinker. For polymers such as MATRIGEL®, for example, a crosslinker is not necessary.

The hydrogel precursor solution can further include an initiator. As known by those skilled in the art hydrogel polymerization can occur in the absence of an initiator. An initiator can, however, induce polymerization and/or decrease the polymerization rate. Suitable initiators are known to those skilled in the art and can be, for example, chemical initiators and photoinitiators. Particularly suitable photoinitiators can be, for example, IRGACURE 2959 photoinitiator (commercially available from Ciba/BASF, Ludwigshafen, Germany), phosphinate initiators (e.g., lithium acylphosphinate salt and lithium phenyl-2,4,6-trimethylbenzoylphosphinate ("LAP")). Polymerization to form the hydrogel can also be performed by temperature change.

In another aspect, the hydrogel precursor solution can include a ligand as described herein. The density (concentration) of the ligand in an individual hydrogel spot of a hydrogel array can be controlled by altering the concentration of the ligand in the hydrogel precursor solution.

In another aspect, hydrogel array can be prepared to include hydrogel spots having a variable modulus. Hydrogel arrays can have a range of moduli. Hydrogel arrays having hydrogel spots with different moduli can be prepared by changing the concentration of the polymer, changing the amount of crosslinking, changing the stoichiometric ratio of the multifunctional polymer (e.g., thiol-polyethylene glycol-thiol (SH-PEG-SH)) to polymer ratio in the hydrogel precursor solution (see e.g., FIGS. 8, 8A and 8B), changing the physical properties of the polymer backbone, changing the physical properties of the crosslinker and combinations thereof. The modulus can also be varied by changing the physical properties of the polymer backbone and/or the crosslinker. For example, 4-arm PEG of 20 kDa has a longer "arm" length than a 4-arm PEG of 10 kDa. Thus, using a 4-arm PEG of 10 kDa can produce a hydrogel of higher modulus than a 4-arm PEG of 20 kDa (see e.g., Toepke et al. 2013 Macromol. Mater. Eng. 298:699-703, which is hereby incorporated by reference to the extent its disclosure is consistent with the present disclosure).

Suitable ratios can be from about 1:1 to about 4:1 (molar ratio). For example, the hydrogel modulus of a hydrogel using PEG-NB polymer and a dithiol crosslinker can be controlled, for example, by altering the ratio of PEG-NB to dithiol crosslinker by, for example, holding the PEG-NB wt % constant, then adding the crosslinker in a ratio that only crosslinks a portion of the PEG-NB arms such as, for example, about 25% to 100% crosslinking.

In another aspect, the hydrogel precursor solution can further include a cell. Suitable cells are known to those skilled in the art and can be, for example, embryonic stem cells (ESCs), ESC-derived neurons, ESC-derived Neural progenitor cells, ESC-derived astrocytes, ESC-derived microglial cells, ESC-derived endothelial cells, mesenchymal stem cells (MSCs), umbilical vein endothelial cells (UVECs), NIH 3T3 fibroblasts, dermal fibroblasts (DFs), fibrosarcoma cells (HT-1080s), and embryonic stem cells (ESCs), valvular interstitial cells, cardiomyocytes, neurons, pericytes, cancer cells such as, for example, melanoma cells, breast carcinoma cells and glioblastoma cells, hepatocytes, pancreatic beta cells and pancreatic islet cells.

In another aspect, the hydrogel precursor solution can further include a microsphere. Microspheres can contain molecules such as, for example, biomolecules, dyes and other molecules known to those skilled in the art. Microspheres can be degradable microspheres that dissolve or degrade to release the contents of the microsphere.

Following contacting the hydrogel precursor solution with the patterned substrate, a surface-modified substrate is placed onto the hydrogel precursor solution such that the hydrogel precursor solution is located between the patterned substrate and the surface-modified substrate.

The substrates and chemistries described herein above can also be used to form the surface-modified substrate. Preparation of the surface-modified substrate involves the formation of end-functional groups that participates in the polymerization chemistry to covalently immobilize the hydrogel polymer to the surface-modified substrate. The surface-modified substrate can be, for example, mica, glass, silicon, diamond and metal oxide surfaces. The surface-modified substrate can be prepared, for example, by creating hydrophobic regions and hydrophilic regions formed by self-assembled monolayers (SAMs) as described herein. The surface-modified substrate can be prepared, for example, using silicon chemistry for a silicon substrate as described herein. The surface-modified substrate can be prepared, for example, using a diamond substrate and creating hydrophilic and hydrophobic regions as described herein. The surface-modified substrate can also be prepared, for example, using a PDMS substrate and creating hydrophilic and hydrophobic regions as described herein. The surface-modified substrate can also be prepared, for example, by functionalizing a surface such as a glass coverslip having a silane monolayer. A particularly suitable surface-modified substrate can be, for example, a glass slide. A particularly suitable method for functionalizing the substrate can be, for example, silanization. The substrate can be surface-modified by activating both sides of the surface in oxygen plasma treatment. Oxygen plasma treatment can increase the number of activated hydroxyl groups on the surface of the substrate. As known by those skilled in the art, a silane monolayer can be prepared with an alkoxysilane that is dissolved in an anhydrous organic solvent such as, for example, toluene. Other suitable alkoxysilanes can be for example, aminosilanes, glycidoxysilanes and mercaptosilanes. Particularly suitable aminosilanes can be, for example, (3-aminopropyl)-triethoxysilane, (3-aminopropyl)-diethoxy-methylsilane, (3-aminopropyl)-dimethyl-ethoxysilane and (3-aminopropyl)-trimethoxysilane. Particularly suitable glycidoxysilanes can be, for example, (3-glycidoxypropyl)-dimethyl-ethoxysilane. Particularly suitable mercaptosilanes can be, for example, (3-mercaptopropyl)-trimethoxysilane and (3-mercaptopropyl)-methyl-dimethoxysilane. Other suitable silanes are commercially available (Sigma Aldrich, St. Louis, Mo.). Preparation of a surface-modified silane substrate can be performed using any silane having a terminal functional group that can participate in click chemistry as described herein. For example, mercaptosilane contains a terminal thiol that can react with the norbornene of the PEG-norbornene. Other suitable functional surface-modified silane substrates can be, for example, acrylates and methacrylates. Following surface-modification of the substrate, non-adhesive self-assembled monolayers are formed on the surface-modified substrate.

After placing the surface-modified substrate onto the hydrogel precursor solution, the method includes polymerizing the hydrogel precursor solution such that polymerized hydrogel attaches to the surface-modified substrate.

After polymerization, the method includes separating the surface-modified substrate from the patterned substrate. Upon separation of the surface-modified substrate from the patterned substrate, the polymerized hydrogel remains attached to the surface-modified substrate to result in the patterned hydrogel array.

In one embodiment, the method can be used to form an array having "spots", "posts" or "islands" of hydrogel (referred to herein as "hydrogel spots") that are surrounded by a background that is substantially free, and even completely free, of hydrogel ("hydrogel-free"). In this embodiment, the hydrogel-free background corresponds to the hydrophobic regions of the patterned substrate and the hydrogel spots correspond to the hydrophilic regions of the patterned substrate. Referring to FIG. 1, the circles would represent the hydrogel spots that would be surrounded by a hydrogel-free region in this embodiment.

In another embodiment, the method can be used to form an array having hydrogel-free pools surrounded by a background of hydrogel (referred to herein as "a hydrogel background"). Referring to FIG. 1, the circles would represent the hydrogel-free pools that would be surrounded by a hydrogel background in this embodiment.

Patterned Hydrogel Arrays

In another aspect, the present disclosure is directed to a patterned hydrogel array including hydrogel spots having variable modulus, variable shear modulus, variable ligand identity, variable ligand density and combinations thereof. Patterned hydrogel arrays including hydrogel spots having variable modulus, variable shear modulus, variable ligand identity, variable ligand density and combinations thereof can be prepared according to the methods described herein above.

The patterned hydrogel array may include hydrogel spots having a variable ligand density (or concentration) of an individual hydrogel spot of the hydrogel array can range up to 7.7 pmol/mm$^2$ for a planar surface. For example, the ligand density can be from 0 pmol/mm$^2$ to about 7.7 pmol/mm$^2$ Suitable ligand density can also be from about 0.25 mM to about 4 mM. Suitable ligands are described herein. The ligand is immobilized to the hydrogel spot as described herein.

The patterned hydrogel array may further include hydrogel spots having a variable ligand identity. For example, at least two different ligands can be incorporated into an individual hydrogel spot. The ligand is immobilized to the hydrogel spot as described herein. Suitable ligands are known to those skilled in the art and can be, for example, any biomolecule containing a cysteine and/or functionalized with a thiol. Thiol-functionalizing of ligands can be performed using commercially available kits (e.g., Traut's Reagent (2-iminothiolane.HCl), Thermo Fischer Scientific, Rockford, Ill.). Suitable ligands can be, for example, proteins, peptides, nucleic acids, polysaccharides, lipids, biomimetic materials and other molecules, and combinations thereof. Particularly suitable proteins can be, for example, adhesion proteins. Particularly suitable adhesion proteins can be, for example, fibronectin, selectin, integrin, cadherin and combinations thereof. Particularly suitable peptides can be, for example, adhesion peptides. As used herein, an "adhesion peptide" refers to an amino acid sequence obtained from an adhesion protein to which cells bind via a receptor-ligand interaction. Examples of particularly suitable peptide sequences are provided in Table 1, below.

TABLE 1

Peptides sequences for hydrogel arrays.

| Name/Source | Sequence | SEQ ID NO |
|---|---|---|
| Fibronectin | RGD | n/a |
| Fibronectin | RGDS | 1 |
| Fibronectin | CRGDS | 2 |
| Fibronectin | GRGDSP | 3 |
| Fibronectin (referred to as "RGD-PHSRN") | CRGD-(G)$_{13}$-PHSRN | 4 |
| Fibronectin | CRGD-(SG)$_5$-PHSRN | 5 |
| Acetylated-CRGDSP | Ac-CRGDSP | 6 |
| Acetylated-GCYGRGDSPG | Ac-GCYGRGDSPG | 7 |
| "Cyclic RGD" | cyclic(RGD{d-Phe}C | 8 |
| non-bioactive scrambled peptide | RDGS | 9 |
| non-bioactive scrambled peptide | CRDGS | 10 |
| Fibronectin | GCYGRGDSPG | 11 |
| Fibronectin | PHSRN | 12 |

TABLE 1-continued

Peptides sequences for hydrogel arrays.

| Name/Source | Sequence | SEQ ID NO |
|---|---|---|
| Fibronectin | GWGGRGDSP | 13 |
| Fibronectin | SIDQVEPYSSTAQ | 14 |
| Laminin | GRNIAEIIKDI | 15 |
| Laminin | DITYVRLKF | 16 |
| Laminin | DITVTLNRL | 17 |
| Laminin | GRYVVLPR | 18 |
| Laminin | GNRWHSTYITRFG | 19 |
| Laminin | GASIKVAVSADR | 20 |
| Laminin | GTTVKYIFR | 21 |
| Laminin | GSIKIRGTYS | 22 |
| Laminin | GSINNNR | 23 |
| Laminin | SDPGYIGSR | 24 |
| Laminin | YIGSR | 25 |
| Collagen I | GTPGPQGIAGQGVV | 26 |
| Collagen I | GTPGPQGIAGQRVV | 27 |
| Collagen II | MNYYSNS | 28 |
| Vitronectin | KKQRFRHRNRKG | 29 |
| Vascular Endothelial Growth Factor-Receptor Binding Peptide | GGGKLTWQELYQLKYKGI | 30 |
| Vascular endothelial growth factor receptor binding peptide (VR-BP) | KLTWQELYQLKYKGI | 31 |
| Bone morphogenetic protein-2 (BMP-2) receptor binding peptide | KIPKASSVPTEL | 32 |
| Bone morphogenic protein receptor-binding peptide | KIPKASSVPTELSAISTLYL | 33 |
| Heparin proteoglycan-binding peptide (HPG-BP) | KRTGQYKL | 34 |
| MMP-degradable crosslinking peptide | KCGGPQGIWGQGCK | 35 |
| MMP-degradable crosslinking peptide | KCGGPQGIAGQGCK | 36 |

In another aspect, ligands can be ligands that are suspected of binding or interacting with a cell to affect cell attachment, spreading, migration, proliferation, and differentiation. This aspect allows for using the patterned hydrogel arrays to specifically screen ligands for effects on the cells such as, for example, cell attachment, spreading, migration, proliferation, and differentiation. Additionally, ligands of unknown function can be immobilized in combination with a cell attachment ligand to screen for changes in cell attachment, spreading, migration, proliferation, and differentiation.

The patterned hydrogel array may further include hydrogel spots having variable moduli. Patterned hydrogel arrays can have a range of stiffness (expressed herein as elastic modulus). For example, hydrogels with different moduli can be prepared by changing the concentration of the polymer and/or changing the stoichiometric ratio of the multifunctional polymer (e.g., the bifunctional polymer thiol-polyethylene glycol-thiol (SH-PEG-SH)) to polymer ratio in the hydrogel precursor solution (see e.g., FIGS. 8, 8A and 8B). Suitable ratios can be from about 1:1 to about 4:1 (molar ratio). Particularly suitable elastic moduli of the hydrogel array can be similar to the elastic modulus of a given tissue type. For example, the hydrogel array can have an elastic modulus similar to brain tissue, which is less than 1 kPa. The hydrogel array can have an elastic modulus similar to healthy breast tissue (as opposed to diseased breast tissue), which is about 1 kPa. The hydrogel array can have an elastic modulus similar to fat tissue, which is about 3 kPa. The hydrogel array can have an elastic modulus similar to muscle tissue, which is about 10 kPa. The hydrogel array can have an elastic modulus similar to healthy lung tissue (as opposed to diseased lung tissue), which is from about 5 kPa to about 30 kPa. The hydrogel array can have an elastic modulus similar to skin, which is from about 30 kPa to about 50 kPa. The hydrogel array can have an elastic modulus similar to fibrotic tissue, which is from about 20 kPa to about 60 kPa.

Hydrogel modulus as well as determining other mechanical features of the hydrogel can be performed using methods known by those skilled in the art. Dynamic mechanical analysis of hydrogels can be performed using an Ares-LS2 rheometer (commercially available from TA Instruments, New Castle, Del.) to evaluate the modulus of the hydrogels. For example, hydrogel samples can be crosslinked in 8.0 mm diameter 1.2 mm depth Teflon wells for 3 seconds using 365 nm UV light at a dose rate of 90 mW cm$^{-2}$. After swelling the samples to equilibrium in phosphate buffered saline and cutting to a final diameter of 8.0 mm, the samples can be loaded onto 8 mm diameter cross-heads and loaded with 0.2 Newtons of normal force. If the samples are not sufficiently robust to withstand 0.2 Newtons of normal force, the cross-heads can be set at a 1.0 mm gap distance. Samples are then sheared by the cross-heads in an oscillatory manner at a constant frequency of 10 Hz. Shear strains can range from about 0.1% to about 20%. Shear stress, shear strain and the elastic moduli can be calculated as follows:

$$\sigma = Tr/\pi r^2/2 \quad \text{(Eq. 1)}$$

Eq. 1: Sample shear stress based on torque (T), sample radius (r) and the sample polar moment of inertia ($\pi r^2/2$).

$$\varepsilon = \Delta\theta tr/L \quad \text{(Eq. 2)}$$

Eq. 2: Sample shear strain based on rotation rate ($\Delta\theta$), time (t), sample radius (r) and sample height (L).

$$G' = \sigma/\varepsilon \cos\delta \quad \text{(Eq. 3)}$$

Eq. 3: Storage modulus (G') of the sample can be calculated by taking the sample stress ($\sigma$) divided by the sample strain ($\varepsilon$) and multiplying by the cosine of the phase angle ($\delta$). A strain average value can be computed by testing using multiple strains.

Patterned hydrogel arrays can also be patterned to have individual hydrogel spots having any desired sizes. Suitable individual hydrogel spot size of the hydrogel array can be small enough to accommodate a single cell, but also large enough to accommodate many cells, for example. Thus, the individual hydrogel spot size of the hydrogel array can have any desired diameter. Particularly suitable individual hydrogel spot sizes of the hydrogel array can be about 10 μm and larger.

Patterned hydrogel arrays can also be patterned to have individual hydrogel spots having any desired height. The height of the hydrogel spots can be determined by the thickness of the spacer placed onto the patterned metal-coated substrate while performing the method. Thus, the hydrogel spots of the patterned hydrogel array can have any desirable height (see e.g., FIG. 6). Suitable heights of the patterned hydrogel array can be from 20 micrometers (μm) to about 1 millimeter, however, patterned hydrogel arrays can be made much higher than 1 millimeter if desired.

In another aspect, the patterned hydrogel array can be further assembled with a microarray add-on (see, FIG. 9) whereby the patterned hydrogel array is prepared with dimensions to accommodate add-ons of any size. Suitable microarray add-ons are commercially available (Grace Bio Labs, Bend, Oreg.). A microarray add-on can allow for the isolation of each individual hydrogel spot and hydrogel-free pool of the hydrogel array such that soluble factor presentation can be controlled. The microarray add-on can include the same number of openings as the number of individual hydrogel spots and hydrogel-free pools of the hydrogel array such that each hydrogel spot and hydrogel-free pool can be independently interrogated with soluble factor presentation. Alternatively, the microarray add-on can have larger openings that can accommodate more than one individual hydrogel spot and more than one individual hydrogel-free pool. For example, a microarray add-on can have openings large enough to accommodate a single hydrogel spot or a single hydrogel-free pool, two hydrogel spots or two hydrogel-free pools, three hydrogel spots or three hydrogel-free pools, four hydrogel spots or four hydrogel-free pools, up to all of the hydrogel spots or hydrogel-free pools of the patterned hydrogel array.

Methods of Screening Molecule-Molecule Interactions using the Patterned Hydrogel Arrays In yet another aspect, the present disclosure is directed to a method for screening for molecule-molecule interactions. The method includes preparing a patterned hydrogel array, wherein the patterned hydrogel array includes at least one ligand; contacting the patterned hydrogel array with a molecule known to or suspected of interacting with the at least one ligand; and analyzing the patterned hydrogel array.

The patterned hydrogel array can be prepared as described herein by contacting a hydrogel precursor solution including at least one ligand with a patterned substrate, wherein the patterned substrate includes a hydrophobic region and a hydrophilic region; placing a surface-modified substrate onto the hydrogel precursor solution; polymerizing the hydrogel precursor solution; and separating the surface-modified substrate from the patterned, whereby the hydrogel attaches to the surface-modified substrate and releases from the patterned substrate to result in the patterned hydrogel array including at least one ligand.

The method can further include assembling the patterned hydrogel array with a microarray add-on as described herein to separate one or more individual hydrogel spots or to separate one or more individual hydrogel-free pools of the patterned hydrogel array such that individual hydrogel spots or individual hydrogel-free pools can be interrogated with a molecule known to or suspected of interacting with the at least one ligand.

The method further includes contacting the hydrogel spots or hydrogel-free pools of the patterned hydrogel arrays with a molecule known to or suspected of interacting with the at least one ligand by including the molecule in a binding solution. As used herein, a "binding solution" refers to a solution developed to allow for investigating the potential interaction between molecules. The binding solution can be further modified to include components designed to strengthen or weaken molecule interactions such as, for example, ionic components, pH components and the like.

The patterned hydrogel array can be analyzed using methods known to those skilled in the art. For example, hydrogel arrays can be analyzed using fluorescence, microscopy, and the like.

Methods of Screening a Cell-Surface Interaction using the Patterned Hydrogel Arrays In another aspect, the present disclosure is directed to a method of screening a cell-surface interaction using the patterned hydrogel arrays as prepared herein to include hydrogel spots having variable densities (moduli), variable ligand identities, variable ligand densities, and combinations thereof. The ligand to be screened using the hydrogel array of the present disclosure can be a ligand that is known or suspected of binding or interacting with a cell. The method can further include assembling the patterned hydrogel array with a microarray add-on as described herein to separate one or more individual hydrogel spots of the hydrogel array such that individual hydrogel spots can be interrogated with soluble factors.

The method further includes contacting a cell with a patterned hydrogel array. As used herein, "contacting a cell" refers to seeding cells onto a patterned hydrogel array for the purpose of analyzing the cells and the hydrogel array. As known by those skilled in the art a cell suspension is typically transferred to a substrate and cells are given sufficient time to adhere to the substrate.

In another embodiment, cells can be incorporated in to the hydrogel of the patterned hydrogel array using a hydrogel precursor solution that includes a polymer, a crosslinker and a cell.

The cells are then cultured for a desired time such as, for example, about one hour to about 30 days. After the desired time, cells can be analyzed by microscopy such as, for example, immunofluorescence microscopy, phase contrast microscopy, light microscopy, electron microscopy and combinations thereof. Cells can be analyzed for cell attachment, cell spreading, cell morphology, cell proliferation, cell migration, cell differentiation, protein expression, and combinations thereof.

Suitable cells can be any cell known by those skilled in the art. Particularly suitable cells can be, for example, embryonic stem cells (ESCs), ESC-derived neurons, ESC-derived Neural progenitor cells, ESC-derived astrocytes, ESC-derived microglial cells, ESC-derived endothelial cells, mesenchymal stem cells (MSCs), umbilical vein endothelial cells (UVECs), NIH 3T3 fibroblasts, dermal fibroblasts (DFs), fibrosarcoma cells (HT-1080s), and embryonic stem cells (ESCs), valvular interstitial cells, cardiomyocytes, neurons, pericytes, cancer cells such as, for example, melanoma cells, breast carcinoma cells and glioblastoma cells, hepatocytes, pancreatic beta cells and pancreatic islet cells.

The method may further include contacting the cell with a soluble molecule by including the soluble molecule in the culture medium in which the cells on the hydrogel spot of the patterned hydrogel array are cultured. Particularly suitable soluble molecules may be growth factors and proteoglycans. Suitable growth factors may be, for example, proteins from the transforming growth factor beta superfamily, fibroblast growth factor family of growth factors, platelet derived growth factor family of growth factors and combinations thereof. Particularly suitable growth factors may be, for example, vascular endothelial growth factor, bone morphogenetic proteins, fibroblast growth factor, insulin-like growth factor and combinations thereof. Suitable proteoglycans may be, for example, proteoglycans with heparin, heparan sulfate, or chondroitin glycosaminoglycan side chains.

The methods and patterned hydrogel arrays of the present disclosure allow for exceptional control over the density of the ligand on the hydrogel spot as well as exceptional control over the identity of the ligand on the hydrogel spot. The stiffness of the hydrogel spot of the hydrogel array can also be controlled. This control allows for screening for specific parameters of substrates for the culture of cells, which may alter and influence the outcome of the cellular response to the substrate and culture environment. The patterned hydrogel arrays of the present disclosure further allow for screening combinations of ligands. Thus, the patterned hydrogel arrays of the present disclosure present a tool to perform high-throughput multivariable biological screens on a single surface for identifying specific parameters of substrates that may alter and influence the outcome of the cellular response to the substrate and culture environment.

The disclosure will be more fully understood upon consideration of the following non-limiting Examples.

EXAMPLES

Materials and Methods
PEG-Norborne Synthesis

Eight-arm poly(ethylene glycol) (PEG) with terminal hydroxyl groups (—OH) and a molecular weight of 20 kDa was purchased from JenKem Technology USA (Allen, Tex.). Anhydrous pyridine, 4-dimethylamino)pyridine (DMAP), 5-norbornene-2-carboxylic acid, diethyl ether, and deuterated chloroform ($CDCl_3$, 99.8%) with 0.03% v/v tetramethylsilane (TMS) were purchased from Sigma Aldrich (St. Louis, Mo.). N,N'-Dicyclohexylcarbodiimide (DCC) and anhydrous dichloromethane (DCM) were purchased from ACROS Organics (Geel, Belgium). SNAKESKIN dialysis tubing having a 3.5K molecular weight cut-off was purchased from Thermo Fisher Scientific (Waltham, Mass.).

Eight-arm PEG-OH was functionalized with norbornene to utilize the thiol-ene chemistry for photopolymerization and immobilization of bioactive ligands (as described in Fairbanks et al. Adv. Mater. 2009, 21:5005-5010; Impellitteri et al. Biomaterials 2012, 33:3475-84; Belair and Murphy Acta Biomater. 2013; and Gould et al. Acta Biomater 2012, 8:3201-3209). The PEG-norbornene (PEG-NB) product of the functionalization reaction was filtered through a medium fritted Buchner funnel to remove salts formed during the reaction. The filtrate was then precipitated in 900 mL cold diethyl ether and 100 mL hexane. The solids were collected on qualitative grade filter paper and air dried overnight. The PEG-NB product was purified by dialysis against 4 L of $dH_2O$ at 4° C. for 72 hours (with water change every 8 hours) using rehydrated SNAKESKIN dialysis tubing to remove residual norbornene acid and subsequently freeze dried.

Norbornene functionalization of >90% was confirmed with 1H nuclear magnetic resonance spectroscopy. Samples were prepared at 6 mg/mL in $CDCl_3$ with TMS internal standard. Free induction decay (FID) spectra were obtained using spectroscopy services provided by the National Magnetic Resonance Facility at Madison on a Bruker Instruments Avance III 500i spectrometer at 400 MHz and 27° C.

Hydrogel Array Formation

Hydrogel arrays used for these experiments were composed of hydrogel spots immobilized on silanized glass substrates. Hydrogel spots were formed using gold surfaces patterned to possess regions with differential wettability, whereby the pattern was defined by an elastomeric stencil. The method of preparing the hydrogel arrays is further described below.

Glass Silanization

Glass coverslips and hydrochloric acid (HCl) solution were purchased from Thermo Fisher Scientific (Waltham, Mass.). Toluene, methanol, ethanol, 3-mercaptopropyl trimethoxysilane (3-MPTS), and dithiothreitol (DTT) were purchased from Sigma Aldrich (St. Louis, Mo.). A low pressure plasma system was purchased from Diener Electronic (Ebhausen, Germany).

Glass coverslips were silanized with 3-MPTS to created substrates presenting thiol groups capable of participating in thiol-ene reaction with PEG-NB and subsequently enable covalent immobilization of PEG-NB hydrogels (Seo et al. Colloids Surf B Biointerfaces 2012, 98:1-6). Liquid-phase silanization was performed as previously described (Seo et al. Colloids Surf B Biointerfaces 2012, 98:1-6; Halliwell et al. Anal Chem 2001, 73:2476-2483; and Cras et al. Biosens Bioelectron 1999, 14:683-688). Coverslips were sonicated for 45 minutes in 1:1 methanol to HCl to remove bulk contaminants Immediately prior to silanization, coverslips were activated by oxygen plasma treatment at 40 sccm and 50 W for 5 minutes on each side to increase the number of activated hydroxyl groups on the surface. Activated coverslips were placed in a coplin jar containing 2.5% v/v 3-MPTS in toluene for 4 hours. Excess silanes were removed from the surface of the coverslips by rinsing with toluene, 1:1 ethanol/toluene, and ethanol and dried with $N_2$ gas. Silanized coverslips were placed in an airtight chamber, purged with $N_2$ gas, and cured at 100° C. for 1 hour to crosslink the silanes coupled to the surface and reduce their susceptibility to hydrolysis. Silanized coverslips were stored in the $N_2$ gas purged chamber and protected from light until use. Prior to use, silanized glass coverslips were treated with 10 mM DTT in PBS for 30 minutes at 37° C. to reduce disulfides formed on the surface and to increase free thiols available at the surface (Vistas et al. Appl Surf Sci 2013, 286:314-318).

Fabrication of Elastomeric Stencils

Silicon wafers were purchased from WRS Materials (San Jose, Calif.). SU-8 100 photoresist was purchased from MicroChem (Newton, Mass.). Sylgard 184 silicone elastomer kit was purchased from Dow Corning Corporation (Midland, Mich.).

Polydimethylsiloxane (PDMS) elastomeric stencils were created using soft lithography as previously described (Jo et al. 2000 J Microelectromechanical Syst. 9:76-81). The layout and geometries for the stencil were drawn using Adobe Illustrated, printed onto transparency films using a high resolution commercial laser printing service provided by ImageSetter (Madison, Wis.). The transparency film was used as a photo mask in combination with conventional photolithography techniques to create master molds with SU-8 negative-tone UV photoresist spin-coated on silicon wafers. To create the PDMS stencil, the curing agent and PDMS pre-polymer solution from the Sylgard elastomer kit were thoroughly mixed in a 1:10 weight ratio, spread onto the master mold, and cured at 80° C. for 6 hours. After curing, the PDMS stencils were peeled off from the master mold, briefly cleaned with ethanol, and dried with $N_2$ gas.

Hydrophobic/Hydrophilic Patterning

Gold-coated test slides (1,000 Å gold on 50 Å titanium metal thin films on 25 mm×75 mm×1 mm glass) were purchased from Evaporated Metal Films (Ithica, N.Y.). Perfluorinated alkanethiol (HS—$(CH_2)_{11}$—O—$(CH_2)_2$—$(CF_2)_5$—$CF_3$) was purchased from ProChimia Surfaces (Sopot, Poland). Hydroxyl-terminated alkanethiol (HS—$C_{11}$—(O—$CH_2$—$CH_2)_3$—OH) was synthesized as previously described (Prime and Whitesides 1993 J. Am. Chem. Soc. 115:10714-10721).

Gold-coated slides were patterned with hydrophobic and hydrophilic self-assembled monolayers (SAMs) of alkanethiolates to form regions with differential wettability. Differential wettability patterning served two purposes simultaneously: 1) defined the geometries of the hydrogel spots and 2) confined the contents of each hydrogel spot in the array. Gold-coated slides were immersed in ethanol and sonicated for ~2 minutes, rinsed with ethanol, and dried with $N_2$ gas to remove contaminants and gold oxide layers. Gold-coated slides were immersed in a 1 mM perfluorinated alkanethiol in ethanol solution for ≥2 hours to allow for perfluorinated alkanethiolate SAMs (fluoraSAMs) formation. After fluoraSAMs formation, fluoraSAMs gold-coated slides were cleaned with ethanol and dried with $N_2$ gas. To define hydrophilic regions on the substrate, PDMS stencils were placed on the fluoraSAMs gold-coated slides to selectively protect areas of the slides from plasma etching. The spatial and geometric patterning of the exposed regions on the fluoraSAMs gold-coated slides were defined by the pattern of the PDMS stencil, which, in turn, defined the geometry and spatial patterning of the hydrogel spots that the arrays could comprise. Exposed regions of the fluoraSAMs gold-coated slides were etched by oxygen plasma treatment at 40 sccm and 50 W for 1 minute. The etched gold-coated slides were cleaned with ethanol and dried with $N_2$ gas and immersed in a 0.1 mM hydroxyl-terminated alkanethiol in ethanol solution for ≥2 hours so that hydrophilic alkanethiolate SAMs ($EG_3SAMs$) were formed in the selectively-etched regions of the gold-coated slides. The resulting gold-coated slides with differential wettability were cleaned with ethanol and dried with $N_2$ gas before hydrogel formation.

Hydrophobic and hydrophilic SAMs formation on the gold-coated slides were confirmed with contact angle measurements (see, FIG. 2B). Static contact angles were measured at room temperature using a contact angle goniometer (DataPhysics Contact Angle System OCA, San Jose, Calif.). A drop of distilled water (3 μL) was placed on the surface and the static contact angle was measured for 3 different samples at five different sites on each sample and averaged.

Hydrogel Spot Polymerization and Immobilization

PEG-NB was functionalized as described above. Bifunctional PEG dithiol (PEG-DT) crosslinker (3.4 kDa) was purchased from Laysan Bio (Arab, Ala.). Irgacure 2959 photoinitiator was purchased from Ciba/BASF (Ludwigshafen, Germany). Cysteine-terminated peptides were purchased from GenScript USA (Piscataway, N.J.). Omnicure Series 1000 UV spot cure lamp (365 nm wavelength), light guide, and collimating adapter were purchased from Lumen Dynamics Group (Ontario, Canada). PDMS spacers with thickness dimensions corresponding to the desired hydrogel spot heights were fabricated using the same procedure as stated above.

Hydrogel precursor solutions were prepared by combining PEG-NB, PEG-DT, peptides, and photoinitiator and diluted to desired concentrations with phosphate buffered saline (PBS) immediately prior to hydrogel spots formation. To form each hydrogel array, a patterned gold-coated slide was rinsed with ethanol and dried with N$_2$ gas, PDMS spacers were placed onto hydrophobic regions of the slide, and hydrogel precursor solutions were spotted onto the hydrophilic regions. A DTT-treated silanized glass coverslip was used to sandwich the hydrogel precursor solutions between the coverslip and the slide. Hydrogel precursor solutions were polymerized by UV-initiated photo-crosslinking for 2 seconds at 90 mW/cm$^2$, with the light penetrating through the glass coverslip. The resulting polymerized hydrogel spots were covalently attached and immobilized onto the coverslip. Recall that the silanization procedure produced glass coverslips that were functionalized with thiol-terminated silanes that were capable of participating in the thiol-ene reaction used for hydrogel precursor solution polymerization, which effectively crosslinked the hydrogel network to the surface-bound silanes. The gold-coated slide was separated from the coverslip, which enabled the glass-immobilized hydrogel spots to cleanly detach from the gold-coated slide. The resulting glass-immobilized hydrogel spots, collectively referred to as the "hydrogel array", was sterilized for 1 hour in 70% ethanol and washed with PBS to remove any remaining unreacted components.

The bioactivity of each hydrogel spot in the array was defined by both the identity and concentration of the peptides incorporated therein. Peptides used in this study were CRGDS (SEQ ID NO:2), CRGD-(G)$_{13}$-PHSRN ("RGD-PHSRN"; SEQ ID NO:4), CRGD-(SG)$_5$-PHSRN (SEQ ID NO:5), Ac-CRGDSP (SEQ ID NO:6), cyclic (RGD{d-Phe}C) (SEQ ID NO:8), and a non-bioactive scrambled peptide CRDGS (SEQ ID NO:10). To modulate the bioactivity of each hydrogel spot, different peptides were added to the hydrogel precursor solutions and, following UV-initiated crosslinking, the resulting polymerized hydrogel networks each presented different immobilized peptides. For all arrays, a total of 4 mM of peptides were incorporated into the hydrogel network. To concurrently change the bioactivity of the hydrogel spots via control of peptide identity and concentration, the desired concentration of the chosen bioactive peptide (containing the "RGD" sequence) was determined and the non-bioactive scrambled peptide CRDGS (SEQ ID NO:10) was supplemented to maintain a total peptide concentration of 4 mM in the hydrogel precursor solution.

The modulus of each hydrogel spot in the hydrogel array was defined by the total concentration of PEG in the crosslinked hydrogel network. Increasing the concentration of PEG-NB in the hydrogel precursor solution resulted in a larger amount of PEG crosslinked into the polymerized network, which resulted in an increase in the compressive modulus (see, FIG. 8).

Example 1

In this Example, a hydrogel array immobilized on a glass substrate was prepared.

A gold substrate was modified with a patterned alkanethiolate self-assembled monolayer (SAMs) to provide isolated hydrophilic regions separated by a surrounding hydrophobic region (as illustrated in FIGS. 1A-1B). As illustrated in FIG. 2A (also shown in FIG. 1A), hydrophobic and hydrophilic SAMs formation on the gold-coated slides were confirmed with contact angle measurements. FIG. 2B provides end views during patterning of a gold substrate at the step before hydrophobic patterning 100; of the substrate having fluoraSAMs 110; of the substrate after etching 120; and of the substrate after hydrophilic patterning 130.

Hydrogel precursor solutions containing all components required for polymerization reactions were deposited onto the hydrophilic SAMs regions of the patterned substrate (see, FIG. 1B). The hydrophilic regions served to both confine the contents of the solutions deposited onto each region and to define the geometries of the resulting polymerized hydrogel. Elastomeric spacers (with thickness dimensions equivalent to the desired hydrogel array height) were placed onto the hydrophobic areas of the patterned slide to define the height of the hydrogel array. A glass substrate, modified by silanization to possess SAMs with end-functional groups capable of participating in the polymerization reaction, was used to sandwich the hydrogel precursor solution. During the UV polymerization, the components of the hydrogel precursor solution formed a crosslinked network as well as formed covalent bonds with the end-function groups on the glass substrate. The polymerized hydrogels removed cleanly from the patterned gold substrate to produce a hydrogel array immobilized on the glass substrate (see, FIG. 3).

Example 2

In this Example, a hydrogel array was used to determine the effects of substrate properties on initial stem cell adhesion.

Figure 9:
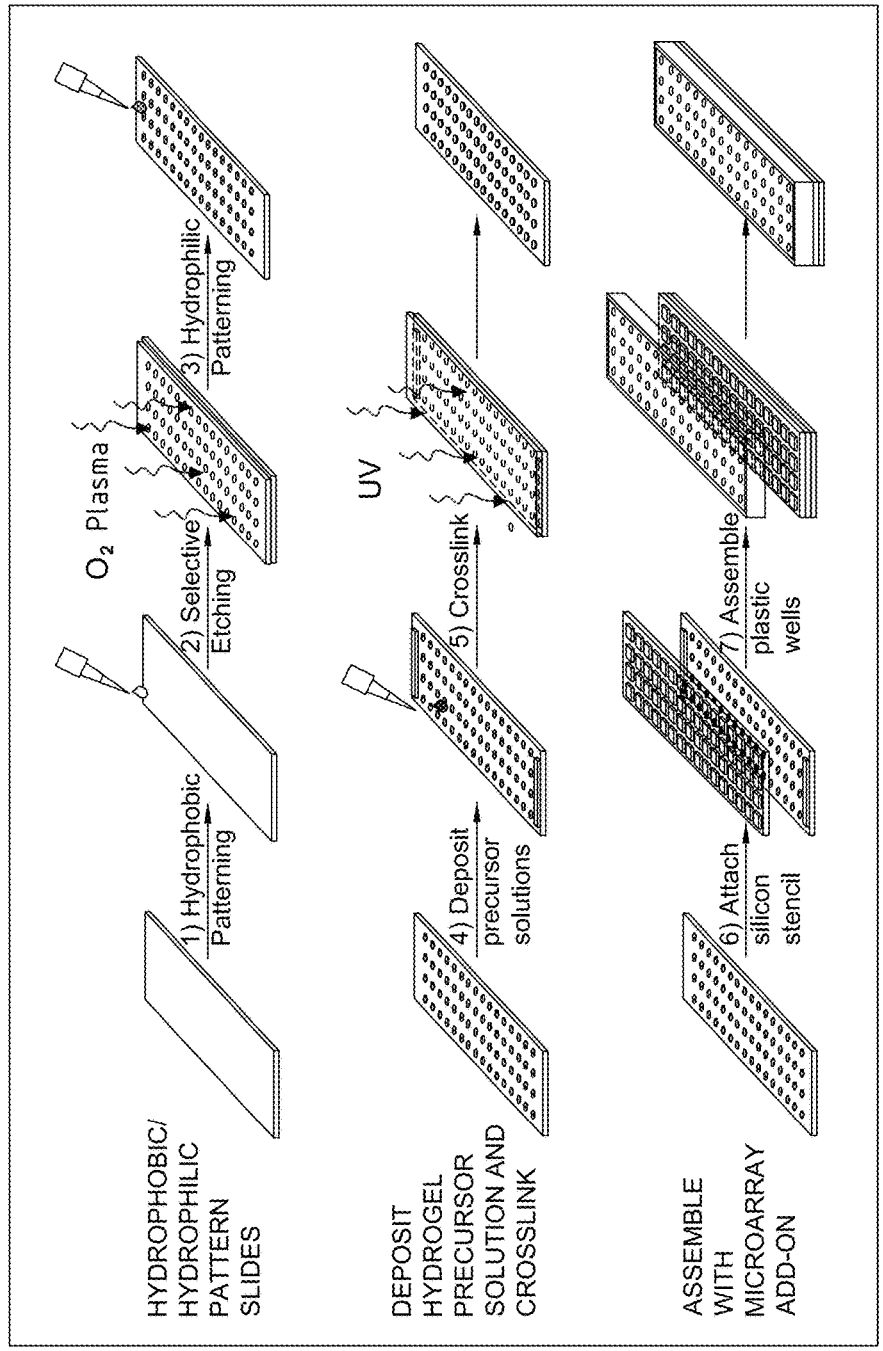
FIG. 9 is a schematic illustrating the steps for preparing a hydrogel array and further assembling the hydrogel array with a microarray add-on using the methods of the present disclosure.
Figure 10A:
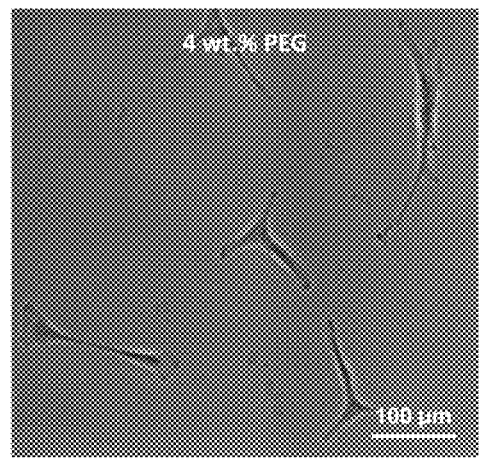
FIG. 10A-10C are photographs of hMSCs cultured on PEG-NB hydrogel arrays prepared using 4 wt. % (FIG. 10A), 6 wt. % (FIG. 10B) and 8 wt. % (FIG. 10C) and presenting linear RGD peptide, as discussed in Example 2.
Figure 10B:
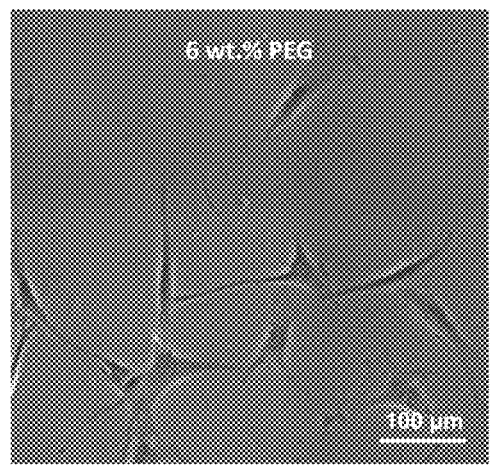
Figure 10C:
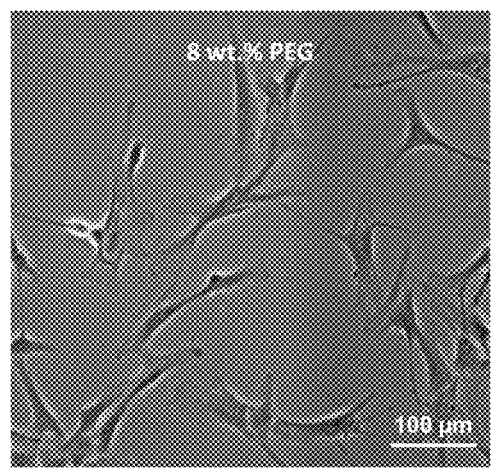

Poly (ethylene glycol) (PEG) hydrogel arrays were formed using patterned hydrophobic/hydrophilic self-assembled monolayers on gold substrates to both define the geometry and confine the contents of each hydrogel spot in the array as described above (see, FIGS. 1A-1B). UV-initiated thiol-ene crosslinking simultaneously polymerized the hydrogel and immobilized the hydrogel spots on the glass to result in the hydrogel array. As illustrated in FIG. 9, hydrogel arrays could be prepared with dimensions compatible with a 64-well microarray add-on (commercially available from Grace Bio-Labs, Bend, Oreg.).

Figure 7A:
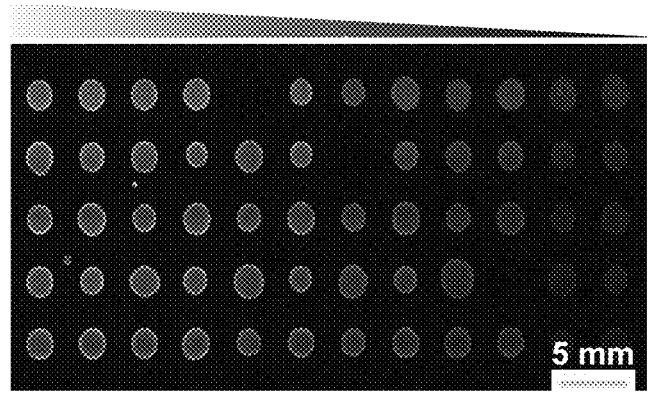
FIG. 7A is a hydrogel array showing differential patterning of individual hydrogel spots by increasing the density of a fluorescently-tagged peptide, as discussed in Example 2.
Figure 7B:
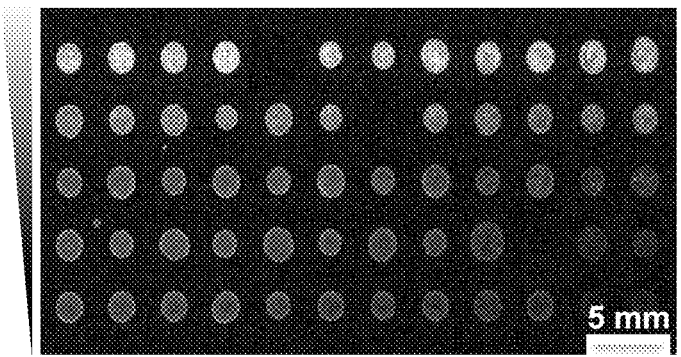
FIG. 7B is the hydrogel array in 7A showing differential patterning of individual hydrogel spots by increasing the density of encapsulated fluorescent microspheres, as discussed in Example 2.
Figure 8:
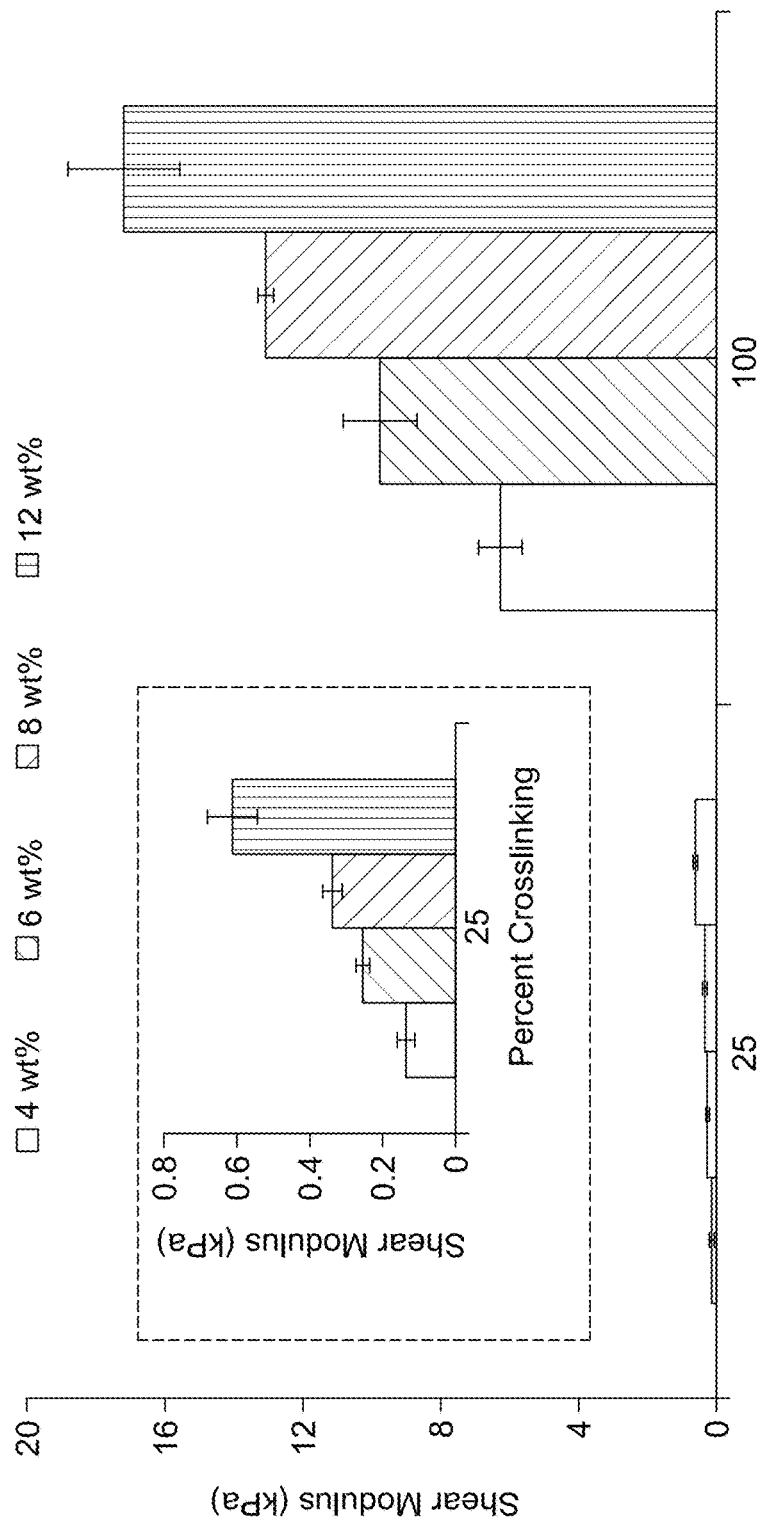
FIG. 8 are graphs illustrating control of the modulus of individual hydrogel spots of a hydrogel array by changing the total concentration of PEG-NB (wt %) and crosslinking molecule (percent crosslinking) at 25% (inset) and 100% crosslinking in the hydrogel precursor solution using the methods of the present disclosure.
Figure 8A:
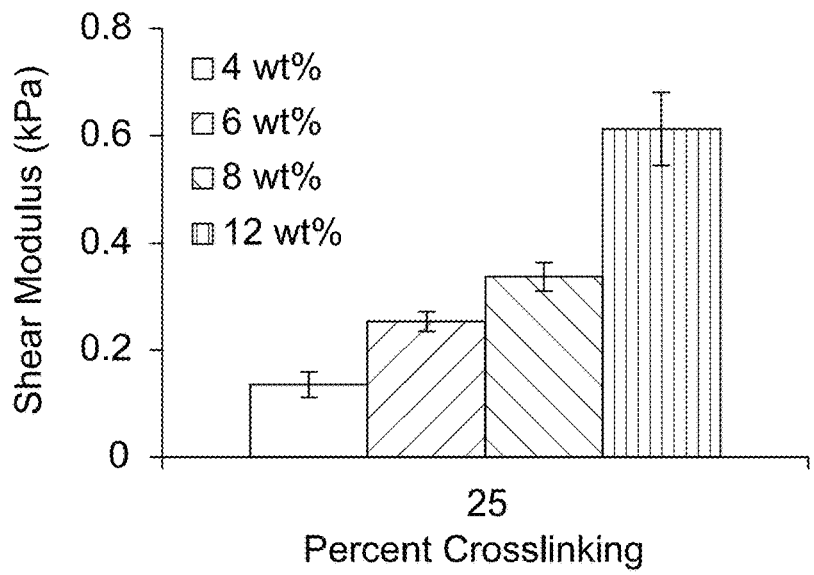
FIG. 8A is a graph illustrating control of the modulus of individual hydrogel spots of a hydrogel array by changing the total concentration of PEG-NB (wt %) and crosslinking molecule (percent crosslinking) at 25% crosslinking in the hydrogel precursor solution using the methods of the present disclosure.
Figure 8B:
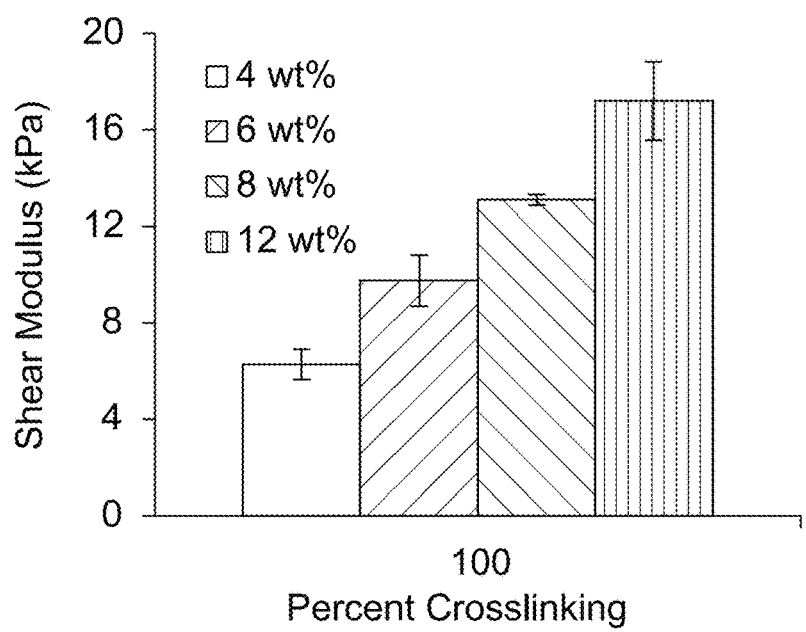
FIG. 8B is a graph illustrating control of the modulus of individual hydrogel spots of a hydrogel array by changing the total concentration of PEG-NB (wt %) and crosslinking molecule (percent crosslinking) at 100% crosslinking in the hydrogel precursor solution using the methods of the present disclosure.
Figure 11A:
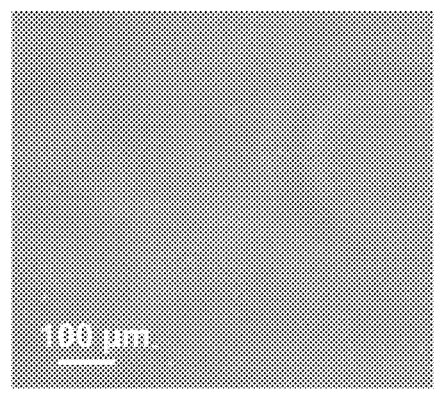
FIG. 11A-11C are photographs of hESCs cultured on PEG-NB hydrogel arrays prepared using 8 wt. % PEG and 75% crosslinking with PEG-dithiol and functionalized with 2 mM of varying fibronectin-derived integrin-binding peptides, as discussed in Example 2.
Figure 11B:
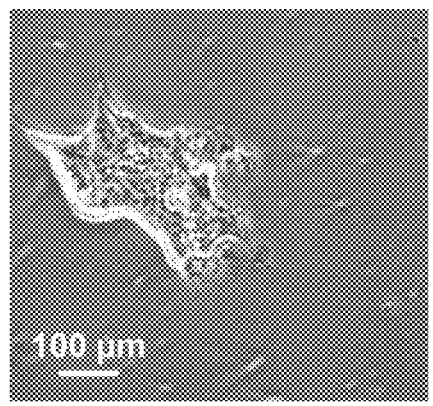
Figure 11C:
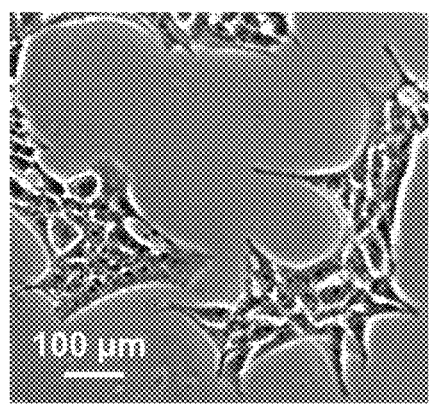

Hydrogel solutions with fibronectin-derived peptides, fluorescent microspheres and a dithiol crosslinker were deposited onto the SAMs and sandwiched with a silanized glass slide. As shown in FIG. 7, individual hydrogel spots of the hydrogel array could be prepared to include varying amounts of fluorescently-tagged peptides (FIG. 7A) as well as varying amounts of fluorescent microspheres (FIG. 7B). Hydrogel solutions with varying PEG or crosslinker concentration were also prepared prior to crosslinking to change the stiffness, peptide identity or peptide concentration (FIGS. 8, 8A and 8B). The resultant arrays (see, FIG. 3) included 2.4 mm diameter, 150 um height posts. Human mesenchymal stem cells (hMSCs) were cultured on posts with varying PEG concentrations (4 wt. %, 6 wt. % and 8 wt. %) to change stiffness and monitored for changes in initial cell adhesion and spreading. Human embryonic stem cells (hESCs) were cultured on PEG-NB hydrogel arrays prepared using 8 wt. % PEG and 75% crosslinking with PEG-dithiol and functionalized with 2 mM of varying fibronectin-derived integrin-binding peptides (FIG. 11A: blank, non-bioactive scrambled peptide RDGS (SEQ ID NO:9), RGDS (SEQ ID NO:2), RGD-PHSRN (SEQ ID NO:4); FIG. 11B: Ac-GCYGRGDSPG (SEQ ID NO:7); and FIG. 11C: cyclic RGD (SEQ ID NO:8)) and monitored for changes in initial cell adhesion and spreading.

Figure 12A:
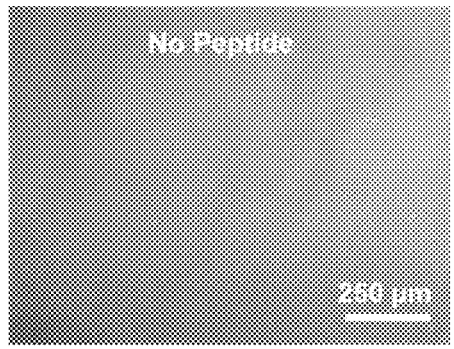
FIG. 12A-12D are photographs of hMSC on PEG-NB hydrogel arrays functionalized with varying integrin-binding peptide densities, as discussed in Example 2.
Figure 12B:
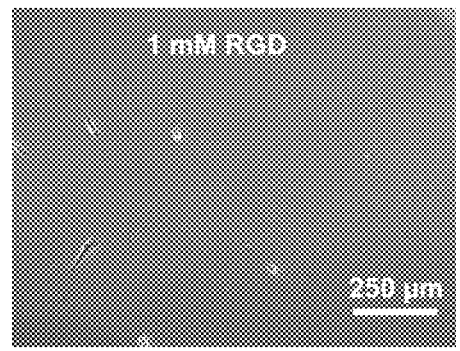
Figure 12C:
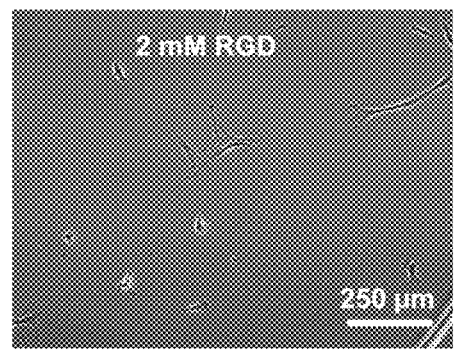
Figure 12D:
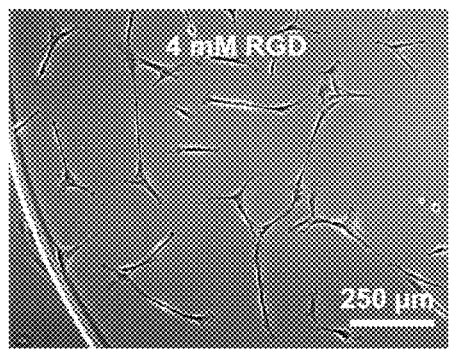

Additionally, hMSCs were seeded on 8-arm PEG-NB (20 kDa) hydrogel arrays (8 wt. % PEG and 25% crosslinking with PEG-dithiol, 3.4 kDa) and functionalized without peptide (FIG. 12A), with 1 mM RGD (FIG. 12B), with 2 mM RGD (FIG. 12C) and 4 mM RGD (FIG. 12D). Cells were allowed to adhere for 24 hours and images were obtained using phase contrast microscopy.

As shown in FIG. 10A-10C, 2D culture of hMSCs demonstrated cell spreading dependence in response to changes in modulus consistent with published observations (see, Engler et al. Cell 126:677 (2006)). 2D culture of hESCs in chemically-defined, albumin-free media demonstrated that cell adhesion was highly specific to peptide-presenting spots. Both hESC cell adhesion and spreading were dependent on the binding affinity of integrin receptors to immobilized peptides (see, FIGS. 11A-11C). Similarly, hMSC cell adhesion and spreading appeared to be dependent on the concentration of peptide density (see, FIGS. 12A-12D). Arrays allowed for changes in hydrogel spot shape, hydrogel spot height (by changing patterned hydrogel spot shapes or adding spacers), hydrogel spot stiffness and hydrogel spot peptide concentrations, and was adaptable for both 2D and 3D cell culture.

These results demonstrate that the method for preparing hydrogel arrays as described herein provides the capability to control stiffness, immobilized ligand identity and ligand concentration (density), and soluble growth factor presentation. The hydrogel arrays of the present disclosure can support cell adhesion and survival and allow for screening complex cell-environment interactions.

Example 3

In this Example, a patterned hydrogel array was used to investigate endothelial cell tubule network formation (termed "tubulogenesis") in vitro.

Figure 13A:
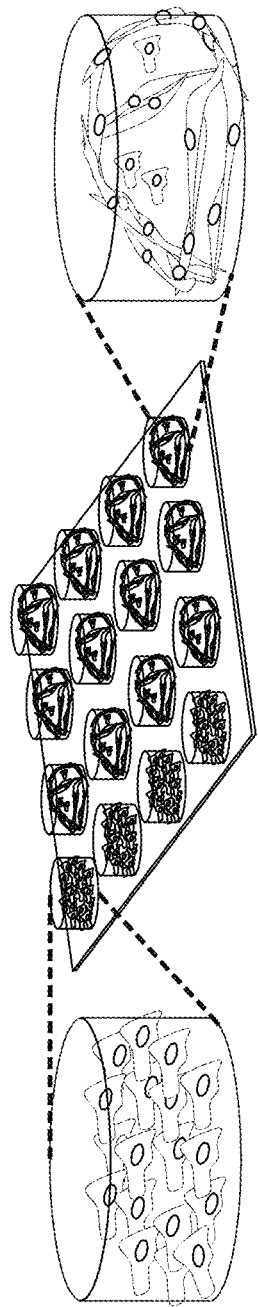
FIG. 13A is a schematic illustration of a hydrogel array seeded with endothelial cells showing enlargements of a hydrogel spot that did not support tubulogenesis and a hydrogel spot that did support tubulogenesis as discussed in Example 3.

Specifically, patterned hydrogel arrays were composed of 8-arm, 20 kDa polyethylene glycol) functionalized with norbenene. As illustrated in the schematic shown in FIG. 13A, the patterned hydrogel arrays included hydrogel spots contained from 30 mg/mL to 60 mg/mL PEG, from 30-70% crosslinking with an MMP-degradable crosslinking peptide (KCGGPQGIWGQGCK, SEQ ID NO:35 or KCGGPQGIAGQGCK, SEQ ID NO:36) and 0.25 mM to 2 mM of a cell adhesive peptide (CRGDS, SEQ ID NO:2). Patterned hydrogel array spots were seeded with human umbilical vein endothelial cells (HUVECs), human induced pluripotent stem cell-derived endothelial cells (iPSC-ECs), and human embryonic stem cell-derived endothelial cells (hESC-ECs) in culture media containing standard growth medium for each cell type (Medium 199 and EGM-2 BULLETKIT™ (Lonza, Basel, Switzerland) for HUVECs, VASCULIFE® and VEGF LifeFactors for iPSC-ECs and hESC-ECs (Lifeline Cell Technology, Frederick, Md.)).

Figure 13B:
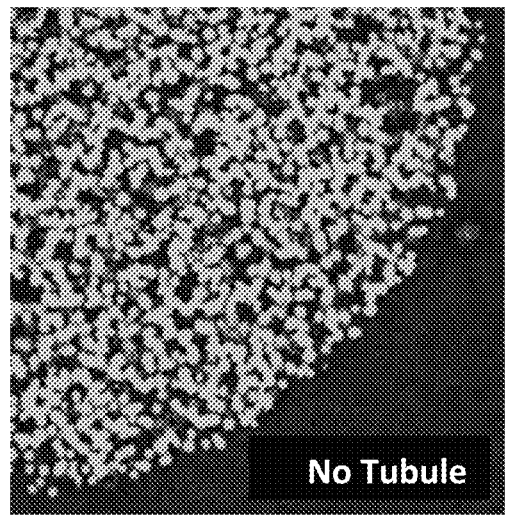
FIG. 13B shows endothelial cells encapsulated in a hydrogel spot that did not support tubulogenesis as discussed in Example 3.
Figure 13C:
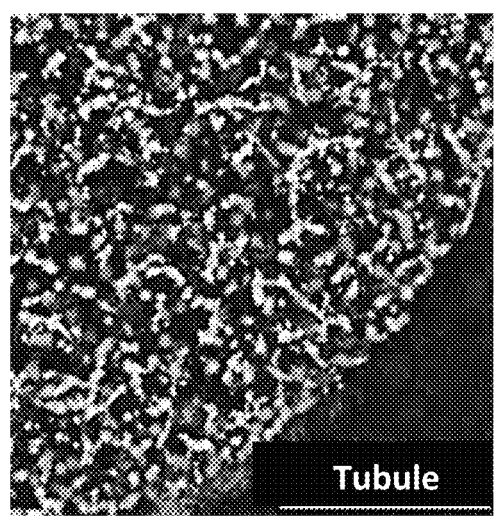
FIG. 13C shows endothelial cells encapsulated in a hydrogel spot that supported tubulogenesis as discussed in Example 3.

Hydrogel spots having less than 36 mg/mL PEG, less than 30% MMP-degradable crosslinking peptide and less than 0.25 mM of the cell adhesive peptide did not form tubules (FIG. 13B). The hydrogel spots that contained between 36 mg/mL to 60 mg/mL PEG, 30-70% crosslinking with an MMP-degradable crosslinking peptide and 0.25 mM to 2 mM of the cell adhesive peptide supported of EC tubule formation (FIG. 13C). Networks were first observed at 4 hours for HUVECs and 24 hours for iPSC-ECs, and networks were stable up to 48 hours for HUVECs, up to 21 days for iPSC-ECs, and up to 16 days for hESC-ECs. Furthermore, the persistence of tubule networks was enhanced by incorporating 0.067 mM to 0.267 biochemical sequestering peptides for vascular endothelial growth factor (CKDAPY-EWNFDILdYdAdFdE; SEQ ID NO:37) into hydrogel arrays or by 3D co-culture with support cells (e.g. iPS-derived Fib-2 mesenchymal stromal cells, human brain-derived pericytes, human mesenchymal stem cells).

Hydrogel arrays that promoted network formation of HUVECs (on 2D hydrogels and in 3D hydrogels) and iPSC-ECs (in 3D hydrogels) contained 50% crosslinking with the MMP-degradable peptides and 2 mM of the cell adhesive peptide (CRGDS, SEQ ID NO:2), and network formation of hESC-ECs (in 3D hydrogels) was promoted in conditions that contained 45-50% crosslinking with 2 mM of the cell adhesive peptide (CRGDS, SEQ ID NO:2).

These results demonstrate that hydrogel arrays can support cell viability, proliferation and tubulogenesis.

What is claimed is:

1. A method for preparing a patterned hydrogel array, the method comprising:
contacting a hydrogel precursor solution with a patterned substrate, wherein the patterned substrate comprises a plurality of hydrophobic regions formed by a first self-assembled monolayer and a plurality of hydrophilic regions formed by a second self-assembled monolayer;
placing a surface-modified substrate onto the hydrogel precursor solution such that the hydrogel precursor solution is located between the patterned substrate and the surface-modified substrate;
polymerizing the hydrogel precursor solution, wherein a plurality of hydrogel spots form on the hydrophilic regions of the patterned substrate and attach to the surface-modified substrate; and
separating the surface-modified substrate from the patterned substrate, wherein the plurality of hydrogel spots are attached to the surface-modified substrate to result in the patterned hydrogel array.

2. The method of claim 1 wherein the patterned substrate is selected from the group consisting of a patterned metal-coated substrate, a patterned silicon substrate, a patterned diamond substrate and a patterned polydimethylsiloxane substrate.

3. The method of claim 1 wherein the surface-modified substrate comprises a silanized glass substrate.

4. The method of claim 1 wherein the plurality of hydrogel spots of the patterned hydrogel array comprises a variable modulus, a variable ligand identity, a variable ligand density and combinations thereof.

5. The method of claim 4 wherein the plurality of hydrogel spots of the patterned hydrogel array comprises a modulus of from about 0.1 kPa to about 300 kPa.

6. The method of claim 4 wherein the plurality of hydrogel spots of the patterned hydrogel array comprises a ligand density of from 0 pmol/mm$^2$ to about 7.7 pmol/mm$^2$.

7. The method of claim 1 wherein the hydrogel precursor solution comprises a ligand.

8. The method of claim 7 wherein the ligand is selected from the group consisting of a protein, a peptide, a nucleic acid, a polysaccharide, a lipid, and combinations thereof.

9. The method of claim 1 wherein the plurality of hydrogel spots of the patterned hydrogel array comprises a height of from about 20 micrometers (µm) to about 1 millimeters (mm).

10. A method of screening a molecule-molecule interaction comprising:
preparing a patterned hydrogel array, wherein the hydrogel array is prepared by a method comprising:
contacting a hydrogel precursor solution with a patterned substrate, wherein the hydrogel precursor solution comprises at least one ligand and wherein the patterned substrate comprises a plurality of hydrophobic regions and a plurality of hydrophilic regions;
placing a surface-modified substrate onto the hydrogel precursor solution such that the hydrogel precursor solution is located between the patterned substrate and the surface-modified substrate;
polymerizing the hydrogel precursor solution, wherein a plurality of hydrogel spots form on the plurality of hydrophilic regions of the patterned substrate and attach to the surface-modified substrate; and
separating the surface-modified substrate from the patterned substrate, wherein the plurality of hydrogel spots are attached to the surface-modified substrate to result in the patterned hydrogel array;
contacting the patterned hydrogel array with a molecule known to or suspected of interacting with the at least one ligand; and
analyzing the patterned hydrogel array.

11. The method of claim 10 wherein the molecule known to or suspected of interacting with the at least one ligand is selected from the group consisting of a cell, a nucleic acid, a protein, a lipid, a polysaccharide and combinations thereof.

12. The method of claim 10 wherein the plurality of hydrogel spots comprises a modulus of from about 0.1 kPa to about 300 kPa.

13. The method of claim 10 wherein the patterned hydrogel array comprises a ligand that is known or suspected of binding with a cell at a density of from 0 pmol/mm$^2$ to about 7.7 pmol/mm$^2$.

14. The method of claim 10 wherein the patterned hydrogel array comprises a microarray add-on.

15. The method of claim 11 further comprising contacting the cell with a soluble molecule.

16. The method of claim 11 wherein the cell is selected from the group consisting of an embryonic stem cell, an embryonic stem cell-derived neuron, an embryonic stem cell-derived Neural progenitor cell, an embryonic stem cell-derived astrocyte, an embryonic stem cell-derived microglial cell, an embryonic stem cell-derived endothelial cell, a mesenchymal stem cell, an umbilical vein endothelial cell, an NIH 3T3 fibroblast, a dermal fibroblast, a fibrosarcoma cell, a valvular interstitial cell, a cardiomyocyte, a neuron, a pericyte, a cancer cell, a hepatocyte, a pancreatic beta cell, a pancreatic islet cell and combinations thereof.

17. A patterned hydrogel array comprising a surface-modified substrate, wherein the surface-modified substrate comprises a plurality of hydrogel spots covalently attached to the surface-modified substrate, wherein the plurality of hydrogel spots comprises a variable modulus, a variable ligand identity, a variable ligand density and combinations thereof, and wherein the surface-modified substrate does not comprise a hydrophilic region and a hydrophobic region.

18. The patterned hydrogel array of claim 17 wherein the variable modulus is from about 0.1 kPa to about 300 kPa.

19. The patterned hydrogel array of claim 17 wherein the variable ligand density is from 0 pmol/mm$^2$ to about 7.7 pmol/mm$^2$.

20. The patterned hydrogel array of claim 17 further comprising a cell.

* * * * *